United States Patent
Becker et al.

(10) Patent No.: US 11,021,469 B2
(45) Date of Patent: Jun. 1, 2021

(54) INDOLINE SULFONAMIDE INHIBITORS OF DAPE AND NDM-1 AND USE OF THE SAME

(71) Applicants: LOYOLA UNIVERSITY OF CHICAGO, Chicago, IL (US); Board of Regents, The University of Texas System, Austin, TX (US)

(72) Inventors: Daniel Paul Becker, Glenview, IL (US); Tahirah K. Heath, Chicago, IL (US); Cory Reidl, Franklin Grove, IL (US); Walter Fast, Austin, TX (US)

(73) Assignees: LOYOLA UNIVERSITY OF CHICAGO, Chicago, IL (US); Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 16/514,921

(22) Filed: Jul. 17, 2019

(65) Prior Publication Data
US 2019/0337931 A1     Nov. 7, 2019

Related U.S. Application Data

(62) Division of application No. 15/501,489, filed as application No. PCT/US2015/044915 on Aug. 12, 2015, now Pat. No. 10,385,040.

(60) Provisional application No. 62/036,346, filed on Aug. 12, 2014.

(51) Int. Cl.
| | | |
|---|---|---|
| *A61K 31/404* | (2006.01) | |
| *A61K 31/4439* | (2006.01) | |
| *C07D 209/10* | (2006.01) | |
| *C07D 209/08* | (2006.01) | |
| *C07D 401/12* | (2006.01) | |
| *C07D 403/12* | (2006.01) | |

(52) U.S. Cl.
CPC ......... *C07D 403/12* (2013.01); *C07D 209/08* (2013.01); *C07D 209/10* (2013.01); *C07D 401/12* (2013.01)

(58) Field of Classification Search
CPC .............. A61K 31/4439; A61K 31/404; C07D 401/12; C07D 209/10; C07D 209/08; C07D 403/12
See application file for complete search history.

(56) References Cited

U.S. PATENT DOCUMENTS

| | | |
|---|---|---|
| 4,428,881 A | 1/1984 | Hedrich et al. |
| 4,615,966 A | 10/1986 | Borror et al. |
| 2009/0163545 A1 | 6/2009 | Goldfarb |
| 2014/0135318 A1 | 5/2014 | Borzilleri et al. |
| 2014/0179666 A1 | 6/2014 | Woolford et al. |
| 2014/0199707 A1 | 7/2014 | Tavarekere et al. |
| 2014/0221341 A1 | 8/2014 | Maiti et al. |

FOREIGN PATENT DOCUMENTS

| | | |
|---|---|---|
| WO | WO-98/32733 A1 | 7/1998 |
| WO | WO-2006/126939 A1 | 11/2006 |
| WO | WO-2007/067993 A1 | 6/2007 |
| WO | WO-2009/003147 A1 | 12/2008 |
| WO | WO-2009/115515 A1 | 9/2009 |
| WO | WO-2010/141738 A2 | 12/2010 |
| WO | WO-2012/143726 A1 | 10/2012 |
| WO | WO-2012/162365 A1 | 11/2012 |
| WO | WO-2017/011408 A1 | 1/2017 |

OTHER PUBLICATIONS

Barange et al., One-pot synthesis of triazolothiadiazepine 1,1-dioxide derivatives via copper-catalyzed tandem {3+2] cycloaddition/N-arylation, Adv. Synth. Catal., 353:41-8 (2011).
Borror et al., Regioselectivity of electrophilic aromatic substitution: synthesis of 6- and 7-sulfamoylindolines and -indoles, J. Org. Chem., 53:2047-52 (1988).
Gillner et al., Inhibitors of bacterial N-succinyl-L,L-diaminopimelic acid desuccinylase (DapE) and demonstration of in vitro antimicrobial activity, Bioorg. Med. Chem. Lett., 19(22):6350-2 (2009).
Gillner et al., Lysine biosynthesis in bacteria: a metallodesuccinylase as a potential antimicrobial target, J. Biol. Inorg. Chem., 18:155-63 (2013).
Gilvarg, N-Succinyl-L-diaminopimelic acid, J. Biol. Chem., 234:2955-9 (1959).
Grosdidier et al., SwissDock, a protein-small molecule docking web service based on EADock DSS, Nucleic Acids Res., 39(Web Server issue):W270-7 (2011).
Ikan et al., Synthesis in indole series. Chloromethylation and chlorosulfonation of 1-acetyl-5-bromoindoline, J. Chem. Eng. Data, 16:125-6 (1971).
International Preliminary Report on Patentability, International Application No. PCT/US2015/044915, dated Feb. 14, 2017.
International Search Report and Written Opinion, International Application No. PCT/US15/44915, dated Nov. 12, 2015.
Li et al., Simplified captopril analogues as NDM-1 inhibitors, Bioorg. Med. Chem. Lett., 24(1):386-9 (2014).
Ma et al., Asymmetric dipolar cycloaddition reactions: a practical, convergent synthesis of chiral pyrrolidine, Tetrahedron:Asymmetry, 8(6):883-7 (1997).
Muanprasat et al., Identification of new small molecule inhibitors of cystic fibrosis transmembrane conductance regulator protein: in vitro and in vivo studies, Biol. Pharm. Bull., 30(3):502-7 (Mar. 2007).
Pavelka et al., Biosynthesis of diaminopimelate, the precursor of lysine and a component of peptidoglycan, is an essential function of *Mycobacterium smegmatis*, J. Bacteriol., 178(22):6496-507 (1996).
Reidl et al., Design and synthesis of inhibitors of the dimetalloprotease DapE as novel broad-spectrum antibiotics, Abstract presented at American Chemical Symposium San Francisco annual meeting (2014).

(Continued)

*Primary Examiner* — Zohreh A Fay
(74) *Attorney, Agent, or Firm* — Marshall, Gerstein & Borun LLP

(57) ABSTRACT

Indoline sulfonamide compounds that can inhibit DapE and/or bacterial metallo-β-lactamases (MBLs), such as NDM-1, are disclosed. Also disclosed are methods of treating an individual suffering from a bacterial infection using the indoline sulfonamide compounds disclosed herein.

20 Claims, 2 Drawing Sheets

(56) References Cited

OTHER PUBLICATIONS

Roberts et al., Hospital and societal costs of antimicrobial-resistant infections in a Chicago teaching hospital: implications for antibiotic stewardship, Clin. Infect. Dis., 49:1175-84 (2009).
Rolain et al., New Delhi metallo-beta-lactamase (NDM-1): towards a new pandemia?, Clin. Microbiol. Infect., 16(12):1699-701 (2010).
Sanders et al., A prospective cross-screening study on G-protein-coupled receptors: lessons learned in virtual compound library design, J. Med. Chem., 55(11):5311-25 (2012).
Scapin et al., Enzymology of bacterial lysine biosynthesis, Adv. Enzymol. Relat. Areas Mol. Biol., 72:279-324 (1998).
Shalygina et al., Sulfonylalkanoic and sulfonamido carboxylic acids containing N-acylated indoline moiety, Khimiya i Khimicheskaya Tekhnologiya, 47(1):61-6 (2004). [Russian only].
Shalygina et al., Synthesis and properties of 1-acylindolinesulfonamides, Khimiya i Khimicheskaya Tekhnologiya, 47(8):91-6 (2004). [Russian Only].
Uda et al., Selectivity of Inhibition of N-Succinyl-L,L-Diaminopimelic Acid Desuccinylase in Bacteria: The product of dapE-gene Is Not the Target of L-Captopril Antimicrobial Activity, Bioinorg. Chem. Appln., Article ID 306465, 6 pp. (2011).

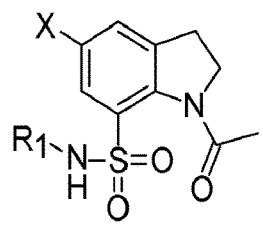

| R¹ | X | Exp. MP (°C) 6 Substituted | Exp. Yield 6 Substituted | logP 6 Substituted | logP 7 Substituted | Docking Results ΔG (kcal/mol) 6 Substituted | Docking Results ΔG (kcal/mol) 7 Substituted |
|---|---|---|---|---|---|---|---|
| R-NH-cyclohexyl | Cl | 224-232 | 79% | 2.9 +/- 0.89 | 2.9 ± 0.88 | -8.44 | -8.51 |
| R-NH-cyclohexyl | Br | 226-228 | 78% | 3.1 +/- 0.92 | 3.7 ± 0.93 | -7.44 | -10.21 |
| R-N-pyrrolidine | Cl | 197-201 | 92% | 1.7 +/- 0.88 | 2.3 ± 0.88 | -8.35 | 9.14 |
| R-N-pyrrolidine | Br | 238-240 | 90% | 1.9 +/- 0.92 | 2.5 ± 0.92 | -8.52 | -9.58 |
| R-N-piperidine | Cl | NA | 79% | 2.3 +/- 0.88 | 3.5 ± 0.89 | -8.14 | -9.14 |
| R-N-piperidine | Br | 212-214 | 70% | 2.4 +/- 0.92 | 3.0 ± 0.92 | -8.43 | -9.08 |
| R-NH-CH(CH₃)₂-like (isobutyl) | Cl | 174-180 | 99% | 2.8 +/- 0.89 | 3.4 ± 0.89 | -7.2 | -10.24 |
| R-NH-CH(CH₃)₂-like (isobutyl) | Br | 190-191 | 99% | 3.0 +/- 0.93 | 3.6 ± 0.93 | -8.96 | -9.46 |
| R-N(CH₂OCH₃)₂ | Cl | 88-93 | 100% | 1.7 +/- 0.94 | 2.3 ± 0.94 | -8.58 | -10.29 |
| R-N(CH₂OCH₃)₂ | Br | 110-111 | 97% | 1.9 +/- 0.97 | 2.5 ± 0.97 | -7.75 | -7.53 |
| R-N(CH₃)₂ | Br | 195-196 | 99% | 2.5 +/- 0.92 | 3.1 ± 0.92 | -8.67 | -9.47 |
| R-N(CH₂CH₃)₂ | Cl | 118-120 | 85% | 3.4 +/- 0.88 | 4.0 ± 0.88 | -8.58 | -9.38 |
| R-N(CH₂CH₃)₂ | Br | NA | NA | 3.6 +/- 0.92 | 4.2 +/- 0.92 | -8.66 | -7.53 |

FIG. 1

| Structure | Halide | mp (°C) | Yield | Col 4 | Col 5 | Col 6 | Col 7 |
|---|---|---|---|---|---|---|---|
|  | Cl | NA | NA | 2.3 +/- 0.89 | 2.9 +/- 0.89 | -8.46 | -9.29 |
|  | Br | 215-220 | 100% | 2.5 +/- 0.93 | 3.1 +/- 0.93 | -8.33 | -10.19 |
|  | Cl | NA | 80% | 3.4 +/- 0.93 | 3.8 +/- 0.93 | -8.34 | -9.75 |
|  | Br | 178-183 | 90% | 3.3 +/- 0.96 | 3.9 +/- 0.96 | 7.94 | -8.66 |
|  | Br | 117-119 | 83% | 2.6 +/- 1.00 | 3.2 +/- 1.00 | -9.41 | -8.51 |
|  | Br | 118-120 | 104% | 3.4 +/- 0.95 | 4.0 +/- 0.95 | -9.01 | -7.44 |
|  | Cl | NA | 107% | 0.97 +/- 0.92 | 1.6 +/- 0.92 | -8.82 | |
|  | Br | 176-182 | 93% | 1.2 +/- 0.95 | 1.8 +/- 0.95 | -8.45 | -9.85 |
|  | Br | 190-193 | 97% | 1.3 +/- 0.94 | 1.9 +/- 0.94 | -9.54 | -10.39 |
|  | Cl | NA | 49% | 2.2 +/- 0.93 | 2.8 +/- 0.93 | -8.39 | -8.99 |
|  | Br | 178-182 | 87% | 2.4 +/- 0.96 | 3.0 +/- 0.96 | -9.25 | -8.68 |

INDOLINE SULFONAMIDE INHIBITORS OF DAPE AND NDM-1 AND USE OF THE SAME

CROSS-REFERENCE TO RELATED APPLICATION

This Application is a Divisional of application Ser. No. 15/501,489 filed on Feb. 3, 2017, which is a U.S. National Phase of International Application No. PCT/US15/44915, which claims the benefit of U.S. Provisional Application 62/036,346 filed on Aug. 12, 2014. The entire contents of each these applications is incorporated herein by reference in its entirety.

STATEMENT OF GOVERNMENT INTEREST

This invention was made with government support under NIH/NIAID 1R15AI085559-01A1 awarded by the National Institutes of Health. The government has certain rights in the invention.

FIELD OF THE INVENTION

The present invention relates to indoline sulfonamide compounds that inhibit bacterial enzymes, such as dapE-encoded N-succinyl-L,L-diaminopimelic acid desuccinylase (DapE) and New Delhi metallo-β-lactamase (NDM-1). The present invention also relates to compositions containing the indoline sulfonamide compounds, and to methods of treating a bacterial infection by administering a therapeutically effective amount of a present indoline sulfonamide compound.

BACKGROUND OF THE INVENTION

Antimicrobial resistance (AMR) is a major, growing health and economic problem worldwide due to the appearance of newer, pathogenic bacterial strains. As the worldwide population began overusing antibiotics in the clinic, for livestock, and in everyday life (e.g. food and hand soap), bacteria began evolving defense mechanisms. As a result, it is estimated that more than 2 million people in the United States are sickened every year with AMR infections with at least 23,000 resulting deaths.

The bacterial enzyme, N-succinyl-L,L-diaminopimelic acid desuccinylase (DapE) is a protein involved in the lysine and diaminopimelic acid (DAP) biosynthetic pathway, and is critical for the synthesis of the bacterial cell wall. See Gillner, et al. Bioorg. Med. Chem. Lett., 2009, 19, 6350-635; Scapin, et al. Adv. Enzymol. Relat. Areas Mol. Biol., 1998, 72, 279-32; Gilvarg, et al. J. Biol. Chem., 1959, 234, 2955-2959. Small molecules that are able to block DapE activity are toxic to bacteria, allowing them to function effectively as antibiotics. Traditional DapE inhibitors, however, are suboptimal because they contain thiol moieties. The thiol moieties are prone to oxidation and also exhibit promiscuous selectivity because they often bind tightly to any zinc-containing enzyme. Also, at least one thiol-containing antimicrobial, captopril, was found to be independent of DapE inhibition. See Creus et al., Bioinorg. Chem. Appl., 2011, 306465.

Metallo-β-lactamases (MBLs) are a diverse set of enzymes that catalyze the hydrolysis of a broad range of β-lactam drugs conferring resistance to the bacteria. New Delhi metallo-β-lactamase 1 (NDM-1) is a zinc-dependent metallohydrolase found in bacteria that confers resistance to commonly-administered antibiotics, including penicillins, cephalosporins, and carbapenems. See Rolain, J. M.; Parola, P.; Cornaglia, G. Clinical Microbiology and Infection 2010, 16, 1699-1701. Horizontal gene transfer has enabled the $bla_{NDM-1}$ gene to spread between species, facilitating the development of multi-drug resistant bacterial strains. Id. Bacteria carrying the $bla_{NDM-1}$ gene have been found on all continents, and consequently, NDM-1 has gained international attention as a clinically relevant pharmaceutical target. Id. Known inhibitors of MBLs, such as thiol-containing inhibitors, are prone to oxidation and challenges with selectivity due to the thiol moiety. See Li et al., Bioorganic & Medicinal Chemistry 24:386-389 (2014).

Therefore, new compounds capable of inhibiting DapE and MBLs (e.g., NDM-1) are greatly needed.

SUMMARY OF THE INVENTION

The present invention is directed to indoline sulfonamide compounds, and to methods of treating a bacterial infection by administration of a present indoline sulfonamide to an individual in need thereof. The indoline sulfonamides inhibit DapE, bacterial metallo-β-lactamase (MBL), or both, and are useful against a wide variety of microorganisms.

The present indoline sulfonamides address the growing problem of antimicrobial resistance. Present technology that are strain specific do not have commercial appeal because they only address only one type of organism, but biofilms are composed of multiple organisms. Killing or preventing association of only one type of bacterium only provides an opportunity for other types of pathogenic organisms, and thus does not solve the problem of antimicrobial resistance. In contrast, the present indoline sulfonamides are effective against a wide variety of microorganisms.

Therefore, the present invention is directed to non-thiol inhibitors of DapE, MBL, or both, which overcome the problems associated with traditional thiol-containing DapE and/or MBL inhibitors and address the problem of antimicrobial resistance.

One aspect of the disclosure provides a method of inhibiting DapE, bacterial metallo-β-lactamase (MBL), or both, in a cell comprising contacting the cell with a compound of Formula (III):

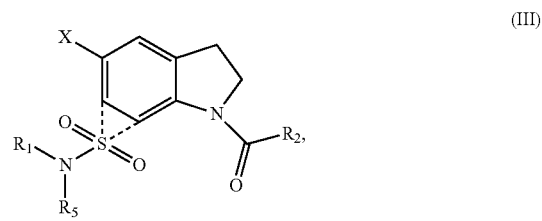

(III)

wherein
the dashed lines indicate that the sulfonamide moiety can be attached to either the 6-position or the 7-position of the indoline sulfonamide compound;
$R_1$ is H, $C_{1-8}$alkyl, $OC_{1-6}$alkyl, $C_{3-8}$cycloalkyl, $C_{3-8}$heterocycloalkyl, $C_{1-6}$alkyleneR$_6$, (C=O)$C_{1-6}$alkyl, aryl, or heteroaryl;
$R_2$ is $C_{1-6}$ alkyl or O—$C_{1-4}$alkyleneR$_6$;
$R_5$ is H, $C_{1-8}$alkyl, $C_{1-6}$alkyleneR$_6$, or $C_{3-8}$cycloalkyl, or $R_1$ and $R_5$ are taken together with the nitrogen to which they are attached to form a 5- to 7-membered ring;
$R_6$ is H aryl, (C=O)OH, (C=O)O$C_{1-3}$alkyl, O$C_{1-3}$alkyl, S$C_{1-3}$alkyl, O(C=O)$C_{1-3}$alkyl; and
X is I, Br, Cl, F, or H.

In some cases, X is H. In other cases, X is Cl. In various cases, X is Br.

In various embodiments, $R_1$ is H. In some cases, $R_1$ is $C_{1-8}$alkyl (e.g., methyl, ethyl, n-propyl, n-butyl, tert-butyl, n-hexyl, or isopentyl). In some embodiments, $R_1$ is $C_{3-8}$cycloalkyl (e.g., cyclopentyl or cyclohexyl). In various cases, $C_{3-8}$heterocycloalkyl (e.g., piperidine). In some embodiments, $R_1$ is $C_{1-6}$alkylene$R_6$. In some of these embodiments, $R_6$ is aryl. In other embodiments, $R_6$ is (C=O)OH or (C=O)O$C_{1-3}$alkyl. In still other embodiments, $R_6$ is O$C_{1-3}$alkyl or S$C_{1-3}$alkyl. For example, $R_1$ can be selected from the group consisting of $CH_2$-phenyl, $(CH_2)_5COOH$, $CH_2(C=O)OCH_3$, $CH_2CH_2(C=O)OCH_3$, $CH(iPr)(C=O)OCH_3$, $CH(CH_2$-phenyl$)(C=O)OCH_3$, $CH(CH_2CH_2SCH_3)(C=O)OCH_3$, $CH_2CH_2OCH_3$, and $CH_2CH_2SCH_3$. In various embodiments, $R_1$ is (C=O)$C_{1-6}$alkyl (e.g., $R_1$ is (C=O)$CH_3$). In some exemplary embodiments, $R_1$ is selected from the group consisting of H, methyl, ethyl, n-propyl, n-butyl, tert-butyl, n-hexyl, isopentyl, cyclopentyl, cyclohexyl, piperidinyl, $OCH_3$, $CH_2$-phenyl, $(CH_2)_5COOH$, $CH_2(C=O)OCH_3$, $CH_2CH_2(C=O)OCH_3$, $CH(iPr)(C=O)OCH_3$, $CH(CH_2$-phenyl$)(C=O)OCH_3$, or $CH(CH_2CH_2SCH_3)(C=O)OCH_3$, $CH_2CH_2OCH_3$, $CH_2CH_2SCH_3$, (C=O)$CH_3$, phenyl, methylpyridine, pyrazine, pyrimidine, isothiazole, and benzothiazole.

In some embodiments, $R_2$ is $C_{1-6}$ alkyl (e.g., methyl or ethyl). In other embodiments, $R_2$ is O—$C_{1-4}$alkylene$R_6$ (e.g., O$CH_2$-phenyl).

In various embodiments, $R_5$ is H. In some cases, $R_5$ is $C_{1-8}$alkyl (e.g., methyl, ethyl, or n-propyl). In some embodiments, $R_5$ is $C_{1-6}$alkylene$R_6$. In some of these embodiments, $R_6$ is aryl. In some cases, $R_6$ is O$C_{1-3}$alkyl. In various cases, $R_6$ is O(C=O)$C_{1-3}$alkyl. For example, $R_5$ can be selected from the group consisting of $CH_2$-phenyl, $OCH_2CH_2OCH_3$, and $CH_2COOCH_3$. In other embodiments, $R_5$ is $C_{3-8}$cycloalkyl (e.g., cyclopentyl or cyclohexyl). In various cases, $R_1$ and $R_5$ are taken together with the nitrogen to which they are attached to form a 5- to 7-membered ring, such as a pyrrolidine, piperidine, azepane, or indoline ring.

In some embodiments, the compound of Formula (III) comprises a compound of Formula (IIIA):

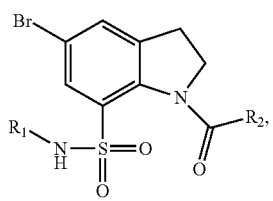
(IIIA)

In various cases, the compound of Formula (IIIA) can include a compound of Formulae (IIIA'), (IIIA"), or (IIIA'''):

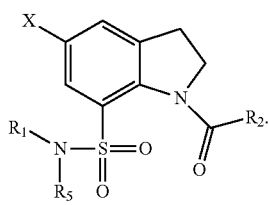
(IIIA')

(IIIA")

(IIIA''')

In some exemplary embodiments, the compound of Formula (IIIA) is selected from the group consisting of:

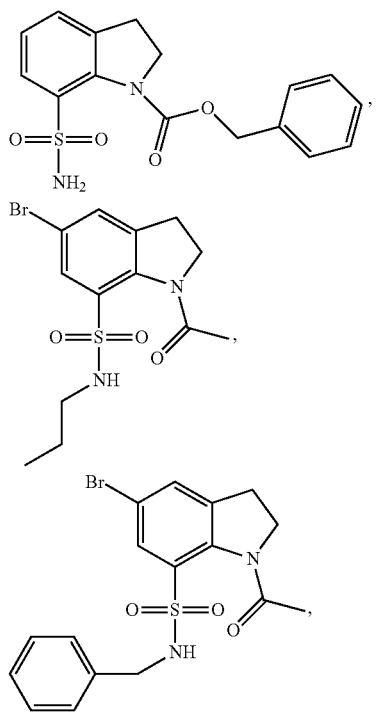

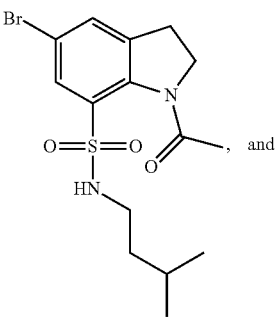

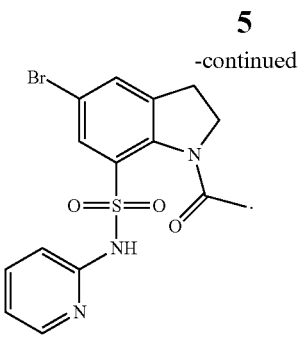
In other embodiments, the compound of Formula (III) comprises a compound of Formula (IIIB):
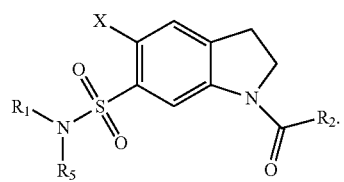
(IIIB)
In various cases, the compound of Formula (IIIB) can include a compound of Formulae (IIIB') or (IIIB"):
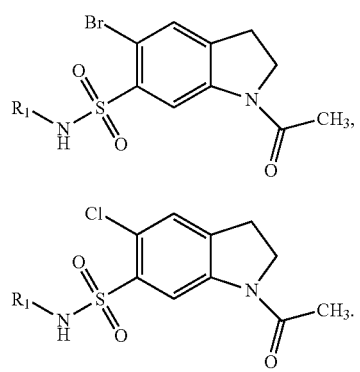
(IIIB')
(IIIB")
In some exemplary embodiments, the compound of Formula (IIIB) is selected from the group consisting of:
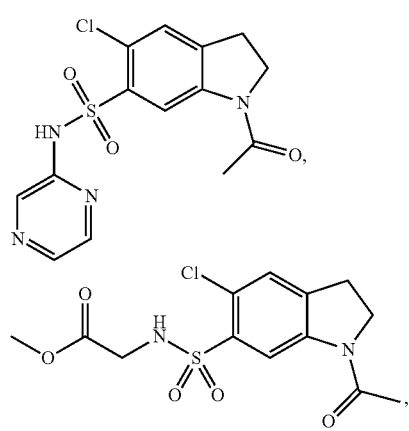
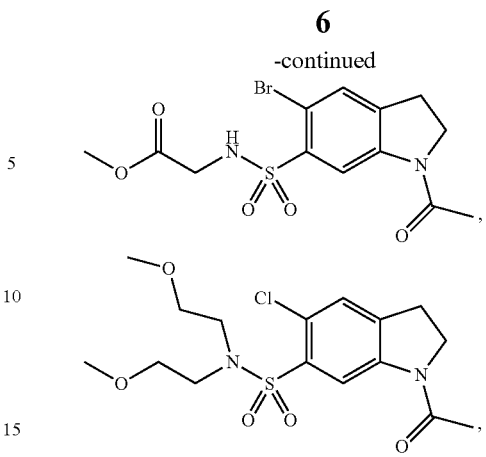
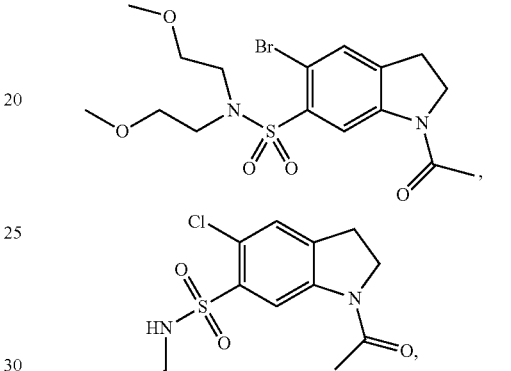
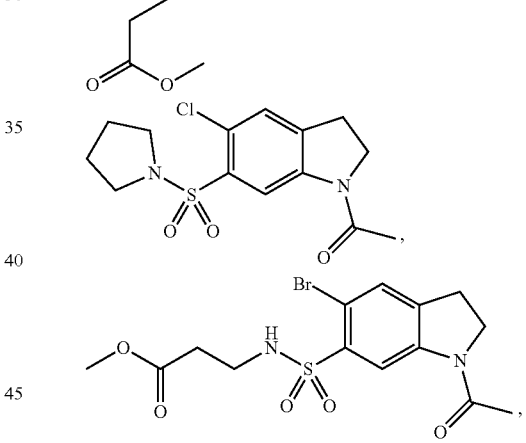
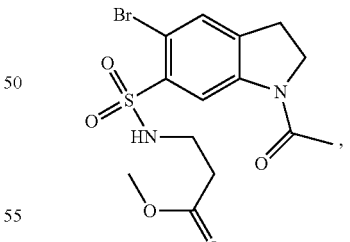
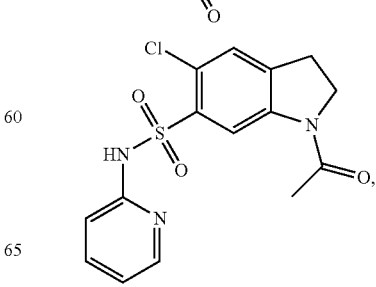

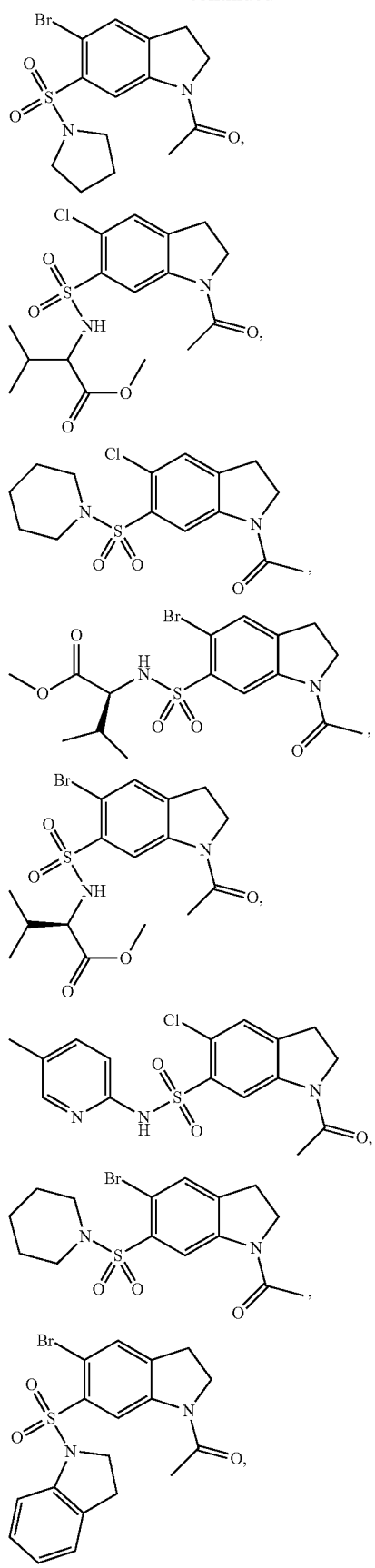
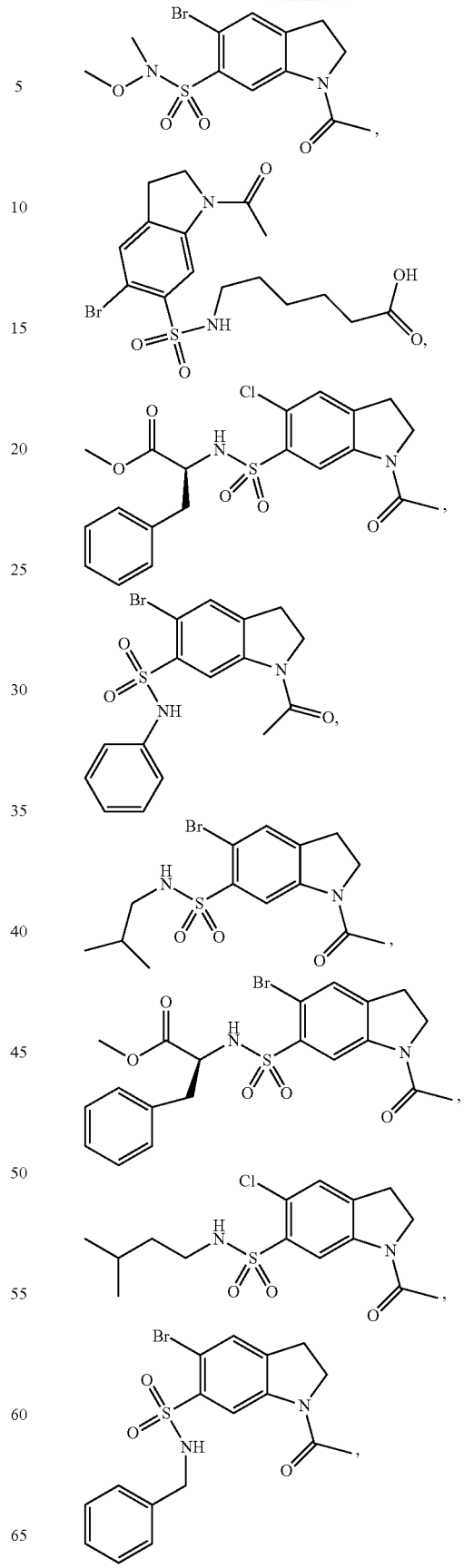

-continued
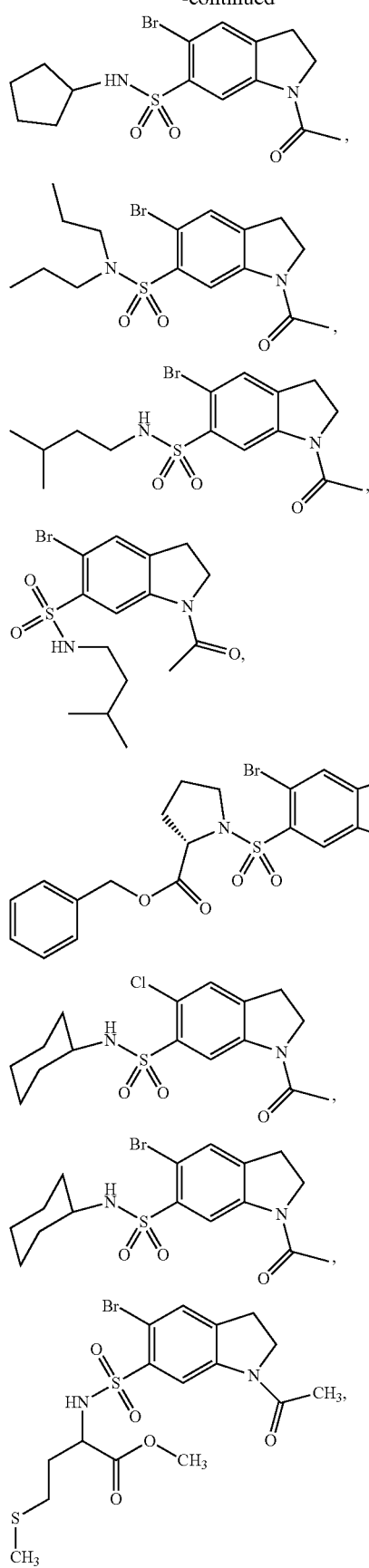
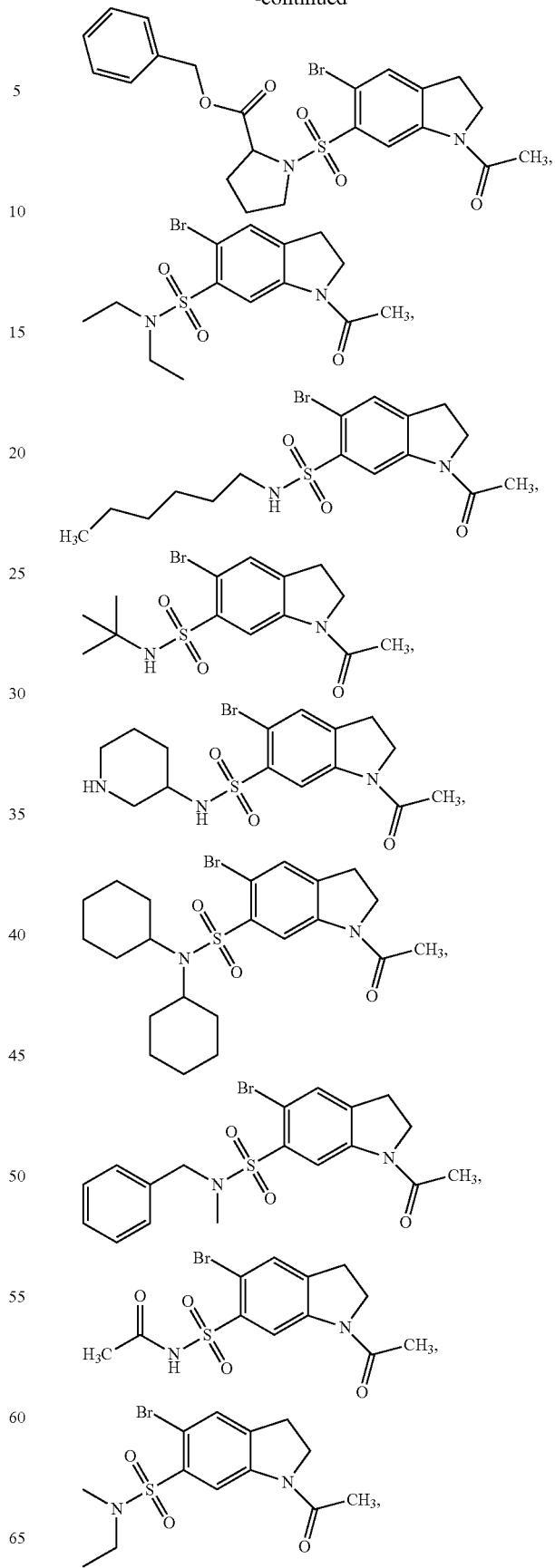

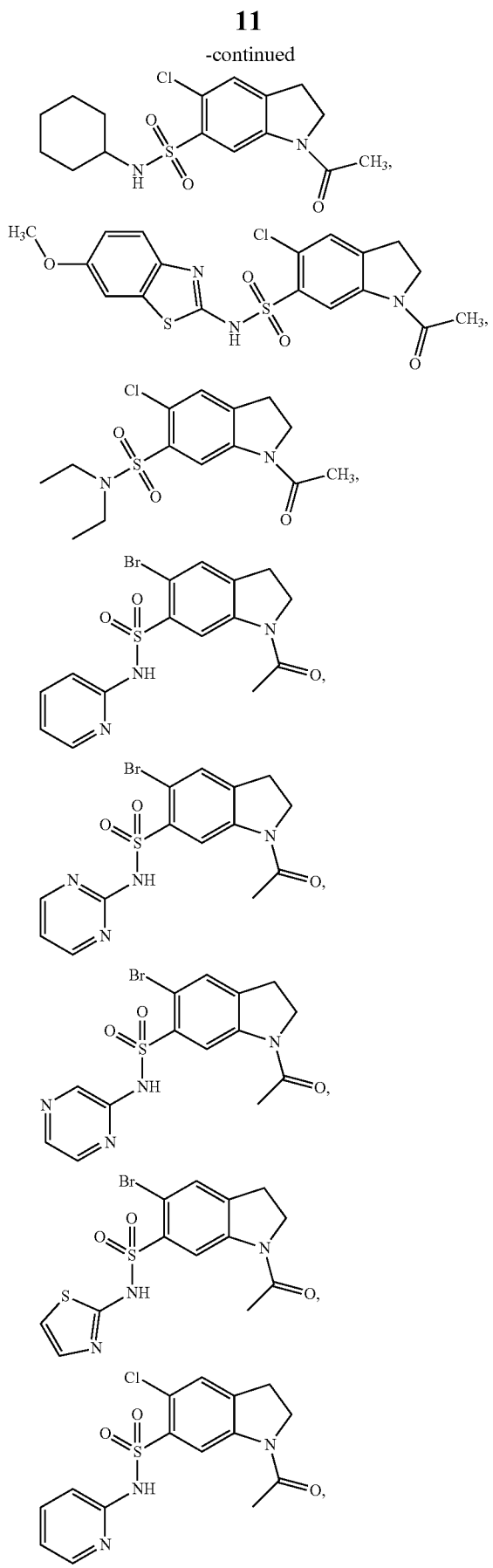

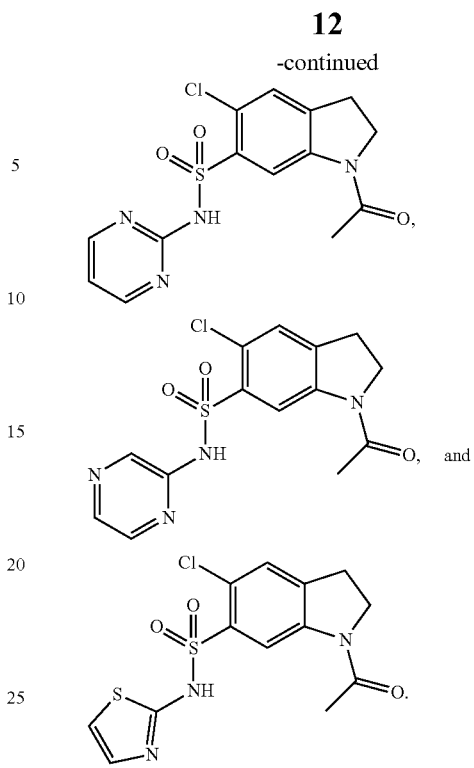

In some cases, the contacting of a cell with a compound of Formula (III) occurs in vivo. In various cases, the contacting comprises administering to a subject in need thereof. In some embodiments, the subject suffers from bacterial infection.

Another aspect of the invention provides method of treating a disease or condition (e.g., a bacterial infection) wherein inhibition of DapE and/or MBL provides a benefit, comprising administering a therapeutically effective amount of a compound of Formula (III), or a pharmaceutically acceptable salt thereof, as previously described herein:

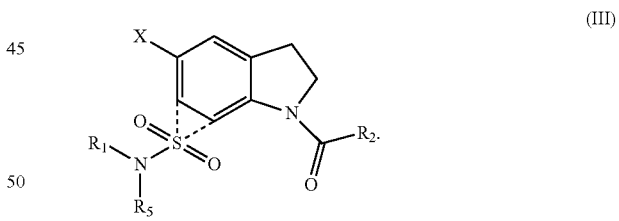

(III)

In some embodiments, DapE is inhibited. In other embodiments, MBL is inhibited. In yet other embodiments, both DapE and MBL are inhibited. In some embodiments, the MBL is selected from the group consisting of NDM-1, IMP-1, and VIM-2. For example, the MBL can be NDM-1.

In the methods disclosed herein, a therapeutically effective amount of a second therapeutic agent (e.g., a β-lactam antibiotic) can be administered along with the inhibitors disclosed herein. The second therapeutic agent can be administered simultaneously or separately.

Another aspect of the disclosure provides a compound having a structure of Formula (IIIA), or a pharmaceutically acceptable salt thereof.

(IIIA)

wherein

R₁ is H, $C_{1-8}$alkyl, $C_{1-6}$alkyleneR₆, aryl, or heteroaryl;

R₂ is $C_{1-6}$ alkyl or O—$C_{1-4}$alkyleneR₆;

R₅ is H, $C_{1-8}$alkyl, $C_{1-6}$alkyleneR₆, or $C_{3-8}$cycloalkyl, or R₁ and R₅ are taken together with the nitrogen to which they are attached to form a 5- to 7-membered ring;

R₆ is aryl, (C=O)O$C_{1-3}$alkyl, O$C_{1-3}$alkyl, O(C=O)$C_{1-3}$alkyl; and

X is Br or Cl.

In some embodiments, the compound of Formula (IIIA) comprises a structure selected from the group consisting of:

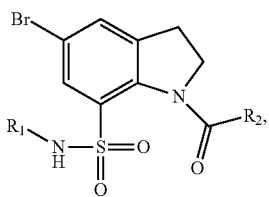

(IIIA')

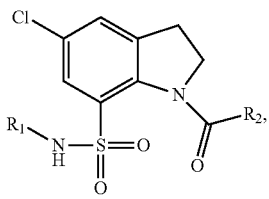

(IIIA")

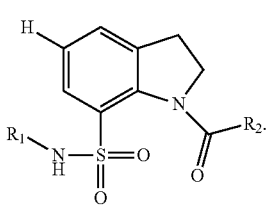

(IIIA''')

wherein

R₁ is selected from the group consisting of H, $C_{1-8}$alkyl, $C_{1-6}$alkyleneR₆, (C=O)$C_{1-6}$alkyl, aryl, and heteroaryl (H, methyl, ethyl, n-propyl, isopropyl n-butyl, isobutyl, tert-butyl, n-pentyl, isopentyl, CH₂-phenyl, and pyridine); and R₂ is $C_{1-6}$ alkyl or O—$C_{1-4}$alkylene-phenyl.

Another aspect of the disclosure provides a pharmaceutical composition of a compound of Formulae (IIIA), (IIIA'), (IIIA"), and/or (IIIA''') and a pharmaceutically acceptable carrier.

Yet another aspect of the disclosure provides a compound selected from the group consisting of

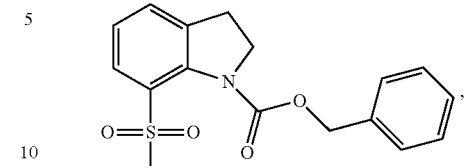

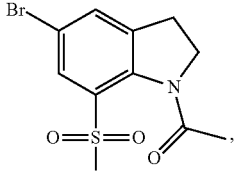

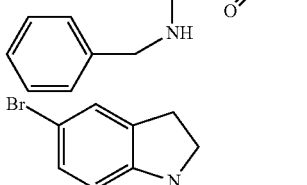

, and

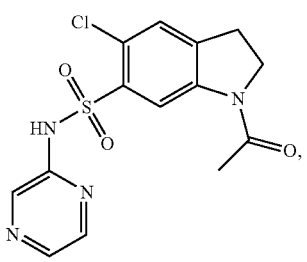

Still another aspect of the disclosure provides a compound selected from the group consisting of

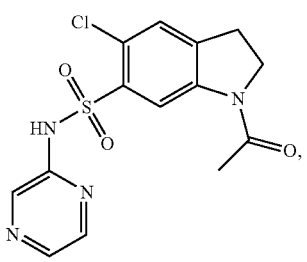

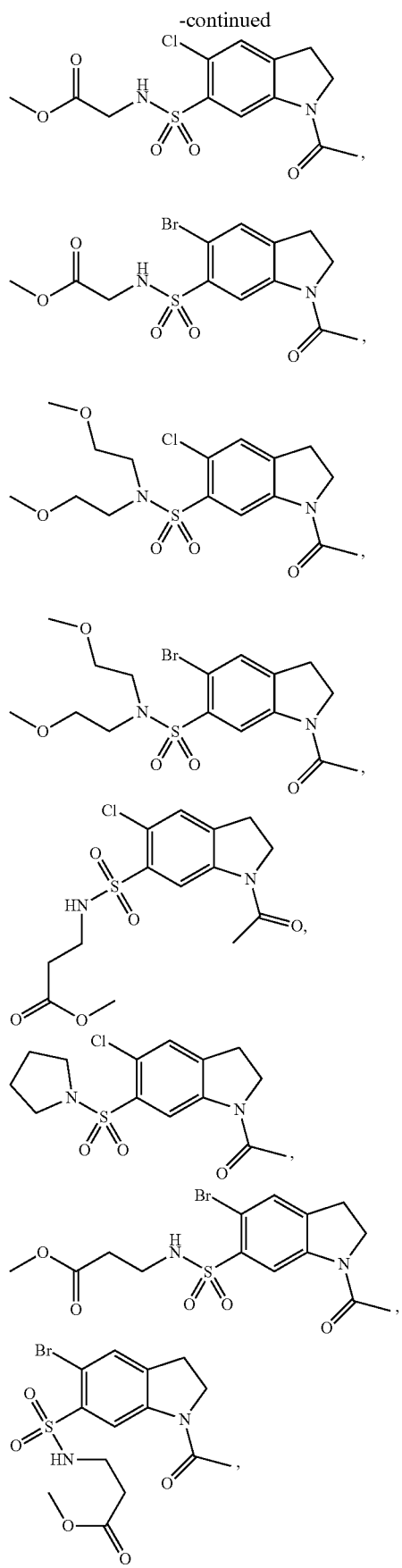
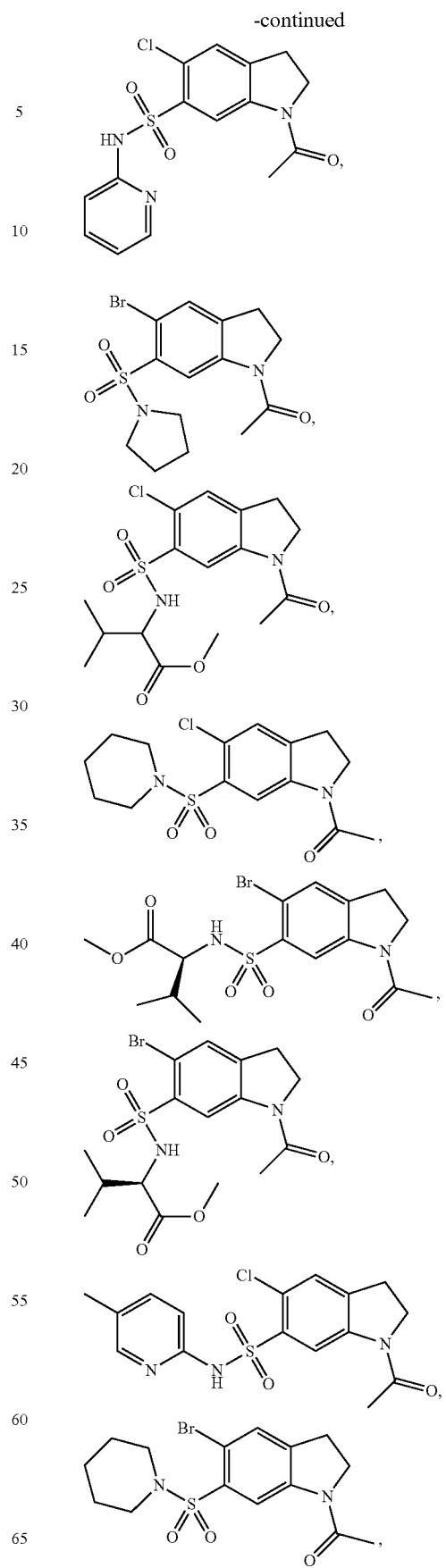

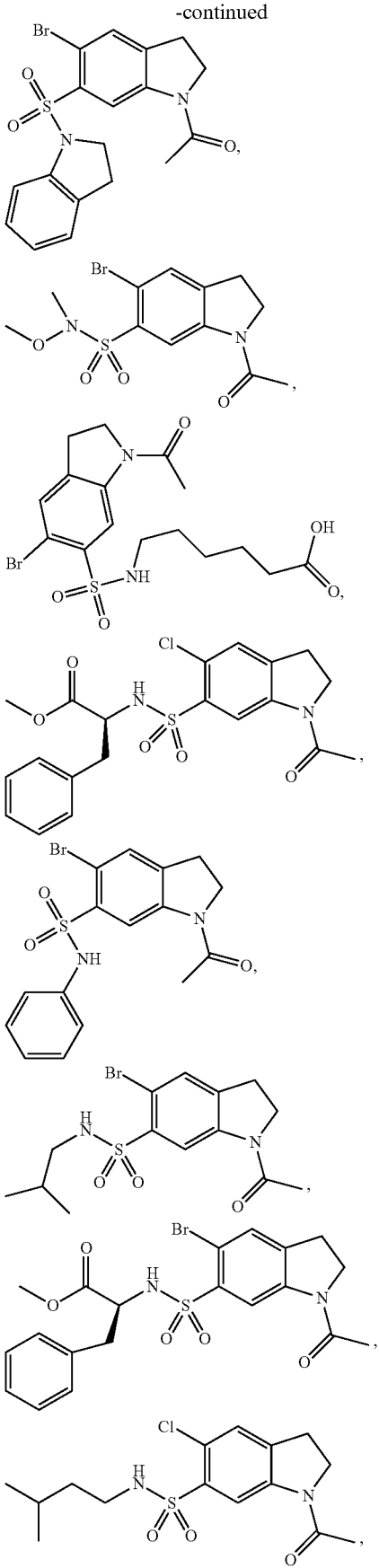
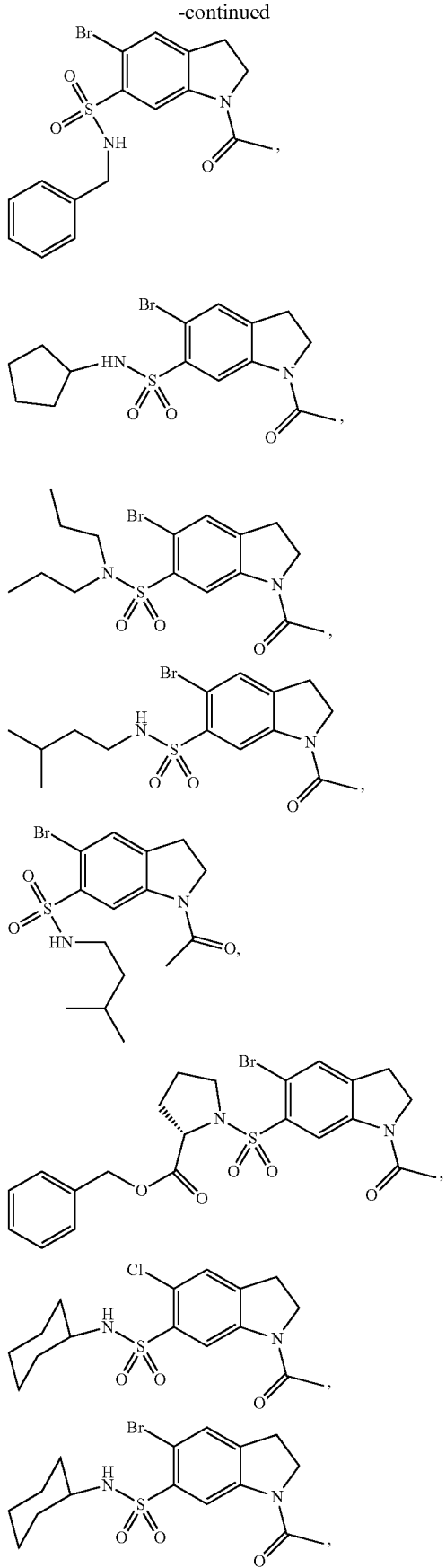

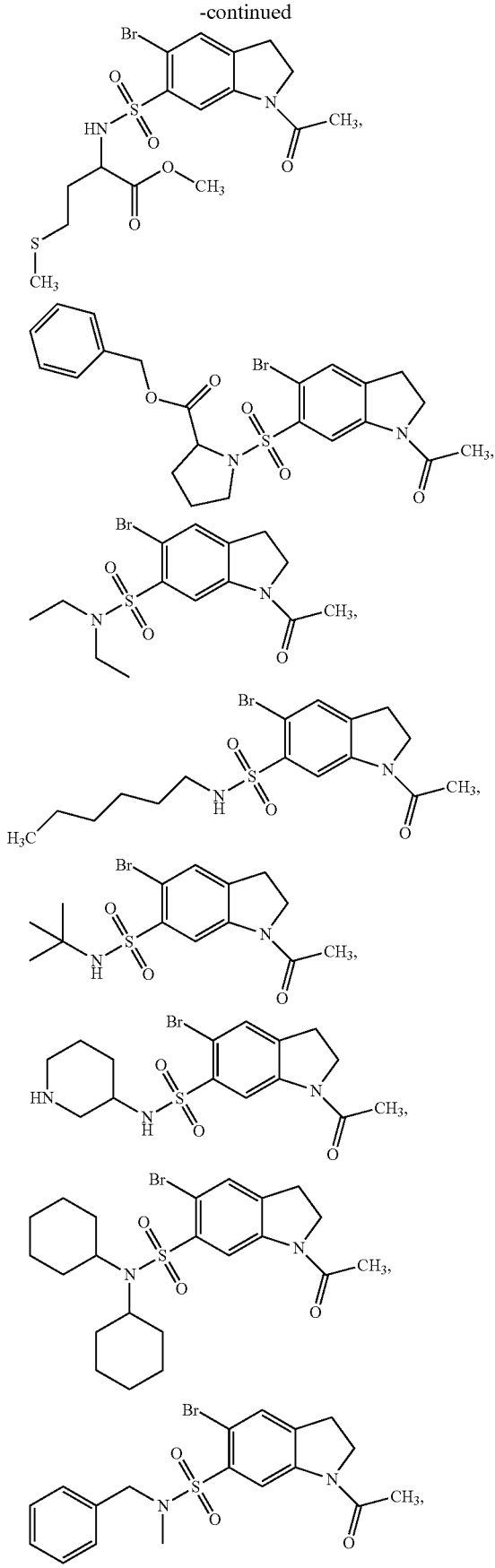
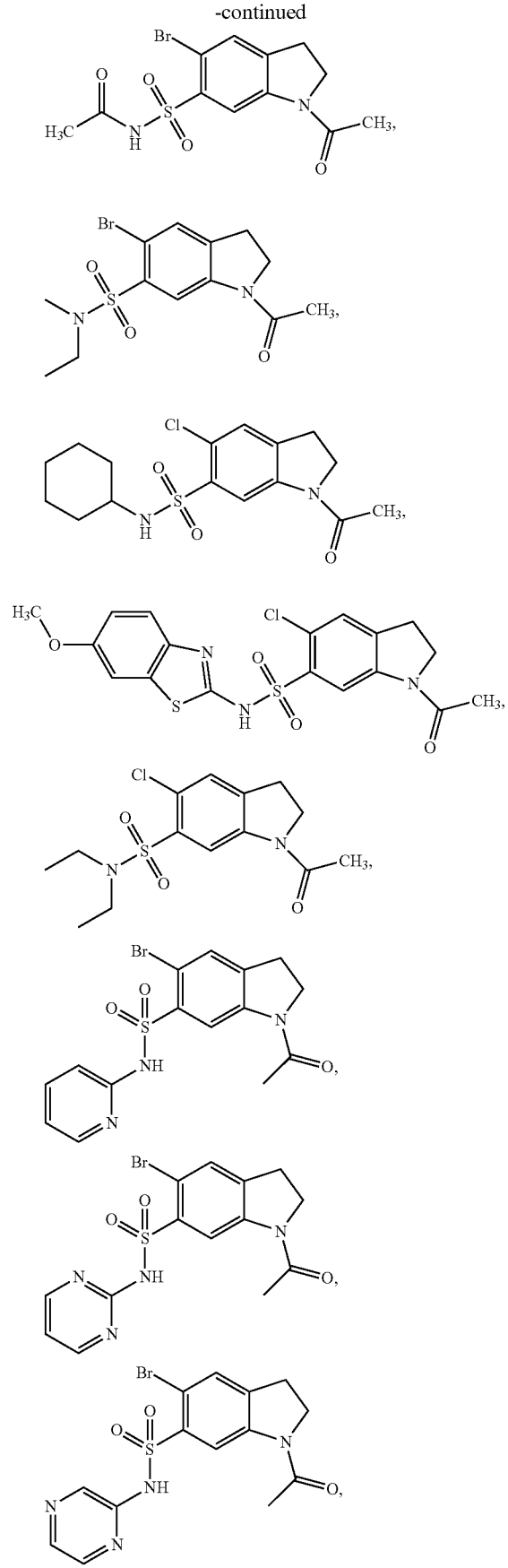

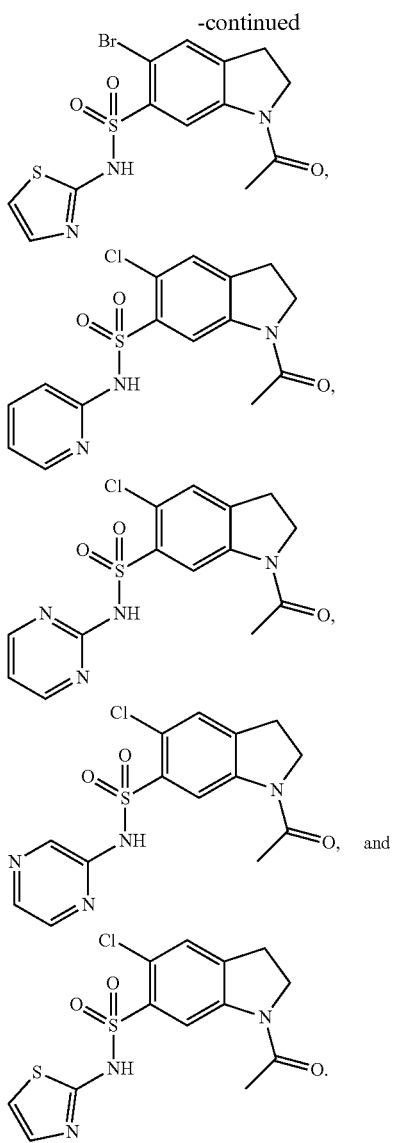

Still another embodiment of the present invention is to provide a kit for human pharmaceutical use comprising (a) a container, (b1) a packaged composition comprising a DapE inhibitor and/or a MBL inhibitor, as described herein, and, optionally, (b2) a packaged composition comprising a second therapeutic agent useful in the treatment of a disease or condition of interest, and (c) a package insert containing directions for use of the composition or compositions, administered simultaneously or sequentially, in the treatment of the disease or condition.

Further aspects and advantages will be apparent to those of ordinary skill in the art from a review of the following detailed description, taken in conjunction with the drawings. While the inhibitors and methods disclosed herein are susceptible of embodiments in various forms, the description hereafter includes specific embodiments with the understanding that the disclosure is illustrative, and is not intended to limit the invention to the specific embodiments described herein.

DETAILED DESCRIPTION OF THE PREFERRED EMBODIMENTS

Figure 1:
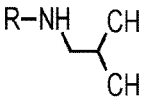
FIG. 1 depicts the results of molecular docking studies using SwissDock (Grosdidier, A.; Zoete, V.; Michielin, O. *Nucleic Acids Res.* 2011, 39, W270-W277.) for the inhibitors described herein to the active site of DapE. Also shown in FIG. 1 are experimental melting points (MP), synthetic yields (Exp. Yield) of the final coupling step (amine plus sulfonyl chloride), and calculated log P values. The Docking Results (delta G) represent more favorable (tighter) binding for the compounds which have more negative values of delta G.
Figure 1:
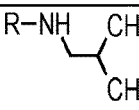
Figure 1:
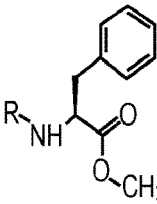
Figure 1:
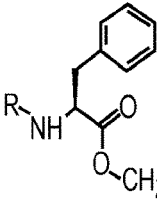
Figure 1:
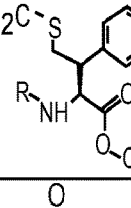
Figure 1:
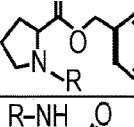
Figure 1:
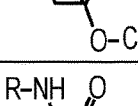
Figure 1:
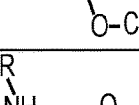
Figure 1:
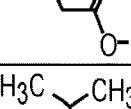
Figure 1:
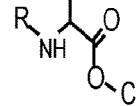
Figure 1:
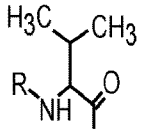

Disclosed herein are 6-, and 7-sulfonamido indoline compounds that inhibit DapE and/or bacterial metallo-β-lactamases (MBLs), such as New Delhi metallo-β-lactamase 1 (NDM-1), and are useful as antibiotics. The present indoline sulfonamide compounds are advantageous over traditional inhibitors of DapE and NDM-1 because they do not rely on a thiol (SH) group for their inhibitory activity. Therefore, they avoid the instability and lack of selectivity of traditional thiol-containing inhibitors of DapE and MBLs, which tend to tightly bind to any zinc-containing enzyme. Furthermore, the 7-substituted sulfonamide indolines provide superior binding to the NDM-1 inhibitor and the DapE inhibitor, and thus, can exhibit superior antibiotic properties.

The compounds disclosed herein can act as inhibitors of DapE. For example, the compounds disclosed herein can have $IC_{50}$ values in a range of about 0.1 nM to about 1000 μM. In various cases, the compounds described herein inhibit DapE with an $IC_{50}$ up to about 100 μM. In some embodiments, the compounds disclosed herein have an $IC_{50}$ value for DapE of less than about 100 μM, or less than about 75 μM, or less than about 50 μM, or less than about 25 μM, or less than about 10 μM, or less than about 5 μM, or less than about 1 μM, or less than about 0.5 μM, or less than about 0.1 μM, or less than about 0.05 μM, or less than about 0.01 μM.

The compounds disclosed herein can act as inhibitors of MBL, such as NDM-1. For example, the compounds disclosed herein can have $IC_{50}$ values in a range of about 0.1 nM to about 1000 μM. In various cases, the compounds described herein inhibit NDM-1 with an $IC_{50}$ up to about 100 μM. In some embodiments, the compounds disclosed herein have an $IC_{50}$ value for NDM-1 of less than about 100 μM, or less than about 75 μM, or less than about 50 μM, or less than about 25 μM, or less than about 10 μM, or less than about 5 μM, or less than about 1 μM, or less than about 0.5 μM, or less than about 0.1 μM, or less than about 0.05 μM, or less than about 0.01 μM.

Definitions

The term "a disease or condition wherein inhibition of DapE provides a benefit" pertains to a condition in which DapE, and/or an action of DapE, is important or necessary, e.g., for the onset, progress, expression of that disease or condition, or a disease or a condition which is known to be treated by DapE inhibitor. An example of such a condition includes, but is not limited to, a bacterial infection. One of ordinary skill in the art is readily able to determine whether a compound treats a disease or condition mediated by DapE for any particular cell type, for example, by assays which conveniently can be used to assess the activity of particular compounds.

The term "a disease or condition wherein inhibition of a MBL provides a benefit" pertains to a condition in which a MBL, and/or an action of MBL, such as NDM-1, is important or necessary, e.g., for the onset, progress, expression of that disease or condition, or a disease or a condition which is known to be treated by a MBL inhibitor. An example of such a condition includes, but is not limited to, a bacterial infection. One of ordinary skill in the art is readily able to determine whether a compound treats a disease or condition mediated by MBL for any particular cell type, for example, by assays which conveniently can be used to assess the activity of particular compounds.

The term "second therapeutic agent" refers to a therapeutic agent different from a DapE and/or MBL inhibitor of structural Formulae (I), (II), (III), (IIIA), (IIIA'), (IIIA"), (IIIA'"), (IIIB), (IIIB'), or (IIIB") and that is known to treat the disease or condition of interest. For example when a bacterial infection is the disease or condition of interest, the second therapeutic agent can be a known antibiotic.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound of the invention to an individual in need of such treatment.

Within the meaning of the invention, "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy.

As used herein, the term "therapeutically effective amount" means an amount of a compound or combination of therapeutically active compounds (e.g., a DapE and/or NDM-1 inhibitor) that ameliorates, attenuates or eliminates one or more symptoms of a particular disease or condition (e.g., bacterial infection), or prevents or delays the onset of one of more symptoms of a particular disease or condition.

As used herein, the terms "patient" and "subject" may be used interchangeably and mean animals, such as dogs, cats, cows, horses, and sheep (i.e., non-human animals) and humans. Particular patients or subjects are mammals (e.g., humans). The terms patient and subject includes males and females.

As used herein, the term "pharmaceutically acceptable" means that the referenced substance, such as a compound of the present invention, or a formulation containing the compound, or a particular excipient, are safe and suitable for administration to a patient or subject. The term "pharmaceutically acceptable carrier" refers to a medium that does not interfere with the effectiveness of the biological activity of the active ingredient(s) and is not toxic to the host to which it is administered.

As used herein, the term "excipient" means any pharmaceutically acceptable additive, carrier, diluent, adjuvant, or other ingredient, other than the active pharmaceutical ingredient (API).

As used herein, "alkyl" refers to straight chained and branched saturated hydrocarbon groups containing one to thirty carbon atoms, for example, one to twenty carbon atoms, or one to ten carbon atoms. The term $C_n$ means the alkyl group has "n" carbon atoms. For example, $C_4$ alkyl refers to an alkyl group that has 4 carbon atoms. $C_1$-$C_7$ alkyl refers to an alkyl group having a number of carbon atoms encompassing the entire range (i.e., 1 to 7 carbon atoms), as well as all subgroups (e.g., 1-6, 2-7, 1-5, 3-6, 1, 2, 3, 4, 5, 6, and 7 carbon atoms). Nonlimiting examples of alkyl groups include, methyl, ethyl, n-propyl, isopropyl, n-butyl, sec-butyl (2-methylpropyl), t-butyl (1,1-dimethylethyl), 3,3-dimethylpentyl, and 2-ethylhexyl. Unless otherwise indicated, an alkyl group can be an unsubstituted alkyl group or a substituted alkyl group.

As used herein, the term "alkylene" refers to a bivalent saturated aliphatic radical. The term $C_n$ means the alkylene group has "n" carbon atoms. For example, $C_{1-6}$alkylene refers to an alkylene group having a number of carbon atoms encompassing the entire range, as well as all subgroups, as previously described for "alkyl" groups.

As used herein, the term "cycloalkyl" refers to an aliphatic cyclic hydrocarbon group containing three to eight carbon atoms (e.g., 3, 4, 5, 6, 7, or 8 carbon atoms). The term $C_n$ means the cycloalkyl group has "n" carbon atoms. For example, $C_5$ cycloalkyl refers to a cycloalkyl group that has 5 carbon atoms in the ring. $C_5$-$C_8$ cycloalkyl refers to cycloalkyl groups having a number of carbon atoms encompassing the entire range (i.e., 5 to 8 carbon atoms), as well as all subgroups (e.g., 5-6, 6-8, 7-8, 5-7, 5, 6, 7, and 8 carbon atoms). Nonlimiting examples of cycloalkyl groups include cyclopropyl, cyclobutyl, cyclopentyl, cyclohexyl, cycloheptyl, and cyclooctyl. Unless otherwise indicated, a cycloalkyl group can be an unsubstituted cycloalkyl group or a substituted cycloalkyl group.

As used herein, the term "heterocycloalkyl" is defined similarly as cycloalkyl, except the ring contains one to three heteroatoms independently selected from oxygen, nitrogen, or sulfur. Nonlimiting examples of heterocycloalkyl groups include piperdine, tetrahydrofuran, tetrahydropyran, dihydrofuran, morpholine, thiophene, and the like. Cycloalkyl and heterocycloalkyl groups can be saturated or partially unsaturated ring systems optionally substituted with, for example, one to three groups, independently selected alkyl, alkyleneOH, C(O)NH$_2$, NH$_2$, oxo (=O), aryl, haloalkyl, halo, and OH. Heterocycloalkyl groups optionally can be further N-substituted with alkyl, hydroxyalkyl, alkylenearyl, and alkyleneheteroaryl.

As used herein, the term "aryl" refers to monocyclic or polycyclic (e.g., fused bicyclic and fused tricyclic) carbocyclic aromatic ring systems. Examples of aryl groups include, but are not limited to, phenyl, naphthyl, tetrahydronaphthyl, phenanthrenyl, biphenylenyl, indanyl, indenyl, anthracenyl, fluorenyl, tetralinyl. Unless otherwise indicated, an aryl group can be an unsubstituted aryl group or a substituted aryl group.

As used herein, the term "heteroaryl" refers to monocyclic or polycyclic (e.g., fused bicyclic and fused tricyclic) aromatic ring systems, wherein one to four-ring atoms are selected from oxygen, nitrogen, or sulfur, and the remaining ring atoms are carbon, said ring system being joined to the remainder of the molecule by any of the ring atoms. Nonlimiting examples of heteroaryl groups include, but are not limited to, pyridyl, pyridazinyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, furanyl, quinolinyl, isoquinolinyl, benzoxazolyl, benzimidazolyl, benzothiazolyl, triazinyl, triazolyl, purinyl, pyrazinyl, purinyl, indolinyl, phthalzinyl, indazolyl, quinolinyl, isoquinolinyl, cinnolinyl, quinazolinyl, naphthyridinyl, pyridopyridinyl, indolyl, 3H-indolyl, pteridinyl, and quinooxalinyl. Unless otherwise indicated, a heteroaryl group can be an unsubstituted heteroaryl group or a substituted heteroaryl group.

The term "thiol" or "sulfhydryl" as used herein refers to a "—SH" group.

As used herein, the term "halo" is defined as fluoro, chloro, bromo, and iodo.

The term "hydroxy" is defined as —OH.

The term "alkoxy" is defined as —OR, wherein R is alkyl.

A "substituted" functional group (e.g., a substituted alkyl, alkyleneyl, cycloalkyl, aryl, or heteroaryl refers to an alkyl, alkyleneyl, cycloalkyl, aryl, or heteroaryl) is a functional, group having at least one hydrogen radical that is substituted with a non-hydrogen radical (i.e., a substitutent). Examples of non-hydrogen radicals (or substituents) include, but are not limited to, alkyl, cycloalkyl, alkenyl, cycloalkenyl, alkynyl, ether, aryl, heteroaryl, heterocycloalkyl, hydroxyl, oxy (or oxo), alkoxyl, ester, thioester, acyl, carboxyl, cyano, nitro, amino, sulfhydryl, and halo. When a substituted alkyl group includes more than one non-hydrogen radical, the substituents can be bound to the same carbon or two or more different carbon atoms.

6-, and 7-Sulfonamido Indoline Compounds

One aspect of the disclosure provides 6-sulfoamido and 7-sulfoamido indolines having a structure (I):

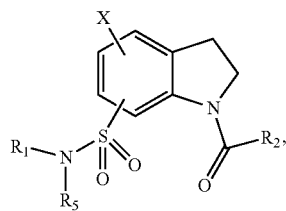

(I)

wherein $R_1$ is alkyl, cycloalkyl, substituted phenyl, substituted benzyl, —(CH$_2$)$_{1-3}$OCH$_3$, —O(CH$_2$)$_{0-3}$CH$_3$, —CH$_2$)$_{0-2}$C(=O)C$_{1-3}$alkyl,

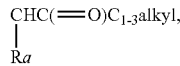

wherein $R_a$ is C$_{1-4}$alkyl, benzyl or —(CH$_2$)$_{1-3}$SCH$_3$; or cycloalkylalkyl;

$R^2$ is alkyl, cycloalkyl, substituted phenyl, cycloalkyl, or NR$_3$R$_4$;

$R_3$ is H or CH$_3$;

$R_4$ is H, alkyl, or cycloalkyl;

or $R_3$ and $R_4$ are taken together with the nitrogen to which they are attached to form a 5-7 membered ring;

$R_5$ is H, alkyl, or (CH$_2$)$_{0-3}$OCH$_3$ or is taken with $R_1$ and the nitrogen atom to which they are attached to form a five to seven-membered ring; and X is halo, OH, R$_4$O, haloalkyl, optionally-substituted aryl, or optionally-substituted heteroaryl, or a pharmaceutically acceptable salt thereof.

In various embodiments, one or more of aryl is phenyl, heteroaryl is pyridyl, haloalkyl is CF$_3$, aryl is substituted with —CO$_2$H, —(CH$_2$)$_{1-3}$CO$_2$H, or —NR$_3$R$_4$.

In one preferred embodiment, the indoline sulfonamide has a 7-sulfonyl group, i.e., a compound of structure (II), where the substituents are as previously described herein.

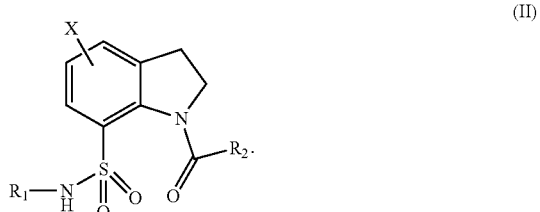

(II)

Also disclosed herein are compounds having a structure (III):

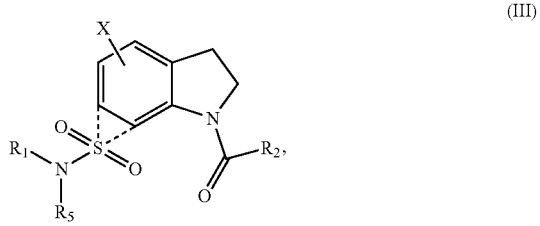

(III)

wherein the dashed lines indicate that the sulfonamide moiety can be attached to either the 6-position or the 7-position of the indoline sulfonamide compound;

$R_1$ is H, C$_{1-8}$alkyl, OC$_{1-6}$alkyl, C$_{3-8}$cycloalkyl, C$_{3-8}$heterocycloalkyl, C$_{1-6}$alkyleneR$_6$, (C=O)C$_{1-6}$alkyl, aryl, or heteroaryl;

$R_2$ is C$_{1-6}$ alkyl or O—C$_{1-4}$alkyleneR$_6$;

$R_5$ is H, C$_{1-8}$alkyl, C$_{1-6}$alkyleneR$_6$, or C$_{3-8}$cycloalkyl, or $R_1$ and $R_5$ are taken together with the nitrogen to which they are attached to form a 5- to 7-membered ring;

$R_6$ is H aryl, (C=O)OH, (C=O)OC$_{1-3}$alkyl, OC$_{1-3}$alkyl, SC$_{1-3}$alkyl, O(C=O)C$_{1-3}$alkyl; and X is I, Br, Cl, F, or H.

In some cases, $R_1$ is H. In some embodiments, $R_1$ is C$_{1-8}$alkyl (e.g., methyl, ethyl, n-propyl, isopropyl, n-butyl, sec-butyl, tert-butyl, n-pentyl, isopentyl, n-hexyl, n-heptyl, or n-octyl). For example, $R_1$ can be methyl, ethyl, n-propyl, n-butyl, tert-butyl, n-hexyl, or isopentyl. In some cases, $R_1$ is C$_{3-8}$cycloalkyl (e.g., cyclopropyl, cyclobutyl, cyclopentyl, cyclohexyl, cycloheptyl, or cyclooctyl). For example, $R_1$ can be cyclopentyl or cyclohexyl. In some cases, $R_1$ is C$_{3-8}$heterocycloalkyl (e.g., piperidine). In various embodiments, $R_1$ is OC$_{1-6}$alkyl, such as OCH$_3$. In various cases, $R_1$ is C$_{1-6}$alkyleneR$_6$. In some of these cases, $R_6$ is aryl (e.g., phenyl). For example, $R_1$ can be CH$_2$-phenyl. In other of these cases, $R_6$ is (C=O)OH. For example, $R_1$ can be (CH$_2$)$_5$COOH. In some of these embodiments, $R_6$ is (C=O)OC$_{1-3}$alkyl (e.g., (C=O)OCH$_3$). For example, $R_1$ can be CH$_2$(C=O)OCH$_3$, CH$_2$CH$_2$(C=O)OCH$_3$, CH(iPr)(C=O)OCH$_3$, CH(CH$_2$-phenyl)(C=O)OCH$_3$, or CH(CH$_2$CH$_2$SCH$_3$)(C=O)OCH$_3$. In some of these embodiments, $R_6$ is OC$_{1-3}$alkyl (e.g., methyl). For example, $R_1$ can be CH$_2$CH$_2$OCH$_3$. In various embodiments, $R_6$ is SC$_{1-3}$alkyl (e.g., methyl). For example, $R_1$ can be CH$_2$CH$_2$SCH$_3$. In some embodiments, $R_6$ is not SC$_{1-3}$alkyl. In some cases, $R_1$ is (C=O)C$_{1-6}$alkyl, such as (C=O)CH$_3$. In various cases, $R_1$ is aryl, such as phenyl. In some embodiments, $R_1$ is heteroaryl. For example, $R_1$ can include pyridine, methylpyridine, pyrazine, pyrimidine, isothiazole, benzothiazole. In some embodiments, $R_1$ can be selected from the group consisting of H, methyl, ethyl, n-propyl, n-butyl, tert-butyl, n-hexyl, isopentyl, cyclopentyl, cyclohexyl, piperidinyl, $OCH_3$, $CH_2$-phenyl, $(CH_2)_5COOH$, $CH_2(C=O)OCH_3$, $CH_2CH_2(C=O)OCH_3$, $CH(iPr)(C=O)OCH_3$, $CH(CH_2$-phenyl$)(C=O)OCH_3$, or $CH(CH_2CH_2SCH_3)(C=O)OCH_3$, $CH_2CH_2OCH_3$, $CH_2CH_2SCH_3$, $(C=O)CH_3$, phenyl, methylpyridine, pyrazine, pyrimidine, isothiazole, and benzothiazole.

In various cases, $R_2$ is $C_{1-6}$ alkyl (e.g., methyl, ethyl, n-propyl, isopropyl, n-butyl, sec-butyl, tert-butyl, pentyl, and hexyl). In some cases, $R_2$ is O—$C_{1-4}$alkyleneR$_6$ (e.g., $OCH_2$-phenyl). For example, $R_2$ can be selected from the group consisting of methyl, ethyl, and $OCH_2$-phenyl.

In some embodiments, $R_5$ is H. In various embodiments, $R_5$ is $C_{1-8}$alkyl or $C_{1-6}$alkyl (e.g., methyl, ethyl, n-propyl, isopropyl, n-butyl, sec-butyl, tert-butyl, pentyl, hexyl, heptyl, octyl). For example, $R_5$ can be methyl, ethyl, or n-propyl. In some cases, $R_5$ is $C_{1-6}$alkyleneR$_6$, and $R_6$ is aryl (e.g., phenyl). For example, $R_5$ can be $CH_2$-phenyl. In various embodiments, $R_5$ is $C_{1-6}$alkyleneR$_6$, and $R_6$ is $OC_{1-3}$alkyl (e.g., $OCH_3$). For example, $R_5$ can be $OCH_2CH_2OCH_3$. In various cases, $R_5$ is $C_{1-6}$alkyleneR$_6$, and $R_6$ is $O(C=O)C_{1-3}$alkyl (e.g., $O(C=O)CH_3$). For example, $R_5$ can be $CH_2COOCH_3$. In some cases, $R_5$ can be $C_{3-8}$cycloalkyl (e.g., cyclopropyl, cyclobutyl, cyclopentyl, cyclohexyl, cycloheptyl, and cyclooctyl). For example, $R_5$ can be cyclopentyl or cyclohexyl. In some embodiments, $R_5$ can be selected from the group consisting of H, methyl, ethyl, n-propyl, $CH_2$-phenyl, $OCH_2CH_2OCH_3$, $CH_2COOCH_3$, cyclopentyl, and cyclohexyl. In some cases, $R_1$ and $R_5$ are taken together with the nitrogen to which they are attached to form an optionally substituted 5- to 7-membered ring (e.g., pyrrolidine, piperidine, azepane, and indoline). In some cases, $R_1$ and $R_5$ are taken together with the nitrogen to which they are attached to form a pyrrolidine ring. In some embodiments, the pyrrolidine ring is substituted. For example, the pyrrolidine ring can be substituted with O—$CH_2$-phenyl or $(C=O)OCH_2$phenyl. In various cases, $R_1$ and $R_5$ are taken together with the nitrogen to which they are attached to form a piperidine ring. In some embodiments, the piperidine ring is substituted. In some embodiments, $R_1$ and $R_5$ are taken together with the nitrogen to which they are attached to form an indoline ring. In some embodiments, at least one of $R_1$ and $R_5$ is a substituent other than H. In some cases, both $R_1$ and $R_5$ are H.

In some embodiments, X is H. In various embodiments, X is not H. In some cases, X is Br or Cl. In various cases, X is Cl. In various embodiments, X is Br. For example, X can be H, Cl, or Br.

In some embodiments, the compound of Formula (III) comprises a 7-sulfonamido group and has a structure of Formula (IIIA):

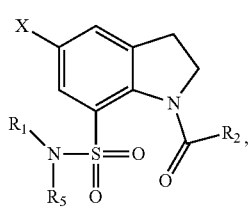

(IIIA)

wherein the substituents are as previously described herein. It has been found that 7-substituted sulfonamide indolines provide superior binding to DapE inhibitors. In some embodiments, $R_1$ is H, $C_{1-8}$alkyl, $C_{1-6}$alkyleneR$_6$, aryl, or heteroaryl; $R_2$ is $C_{1-6}$ alkyl or O—$C_{1-4}$alkyleneR$_6$; $R_5$ is H, $C_{1-8}$alkyl, $C_{1-6}$alkyleneR$_6$, or $C_{3-8}$cycloalkyl, or $R_1$ and $R_5$ are taken together with the nitrogen to which they are attached to form a 5- to 7-membered ring; $R_6$ is aryl, $(C=O)OC_{1-3}$alkyl, $OC_{1-3}$alkyl, $O(C=O)C_{1-3}$alkyl; and X is Br or Cl. In some embodiments, X is Br, and in other embodiments, X is Cl. In some exemplary cases X is Br, $R_2$ is $C_{1-6}$ alkyl or O—$C_{1-4}$alkylene-aryl, and $R_5$ is H, as shown below in Formula (IIIA'), below. In other cases, X is Cl, $R_2$ is $C_{1-6}$ alkyl or O—$C_{1-4}$alkylene-aryl, and $R_5$ is H, as shown below in Formula (IIIA"), below. In still other cases, X is H, $R_2$ is $C_{1-6}$ alkyl or O—$C_{1-4}$alkylene-aryl, and $R_5$ is H, as shown below in Formula (IIIA'''), below.

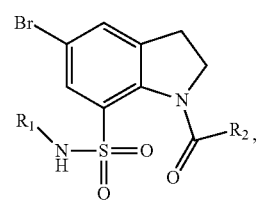

(IIIA')

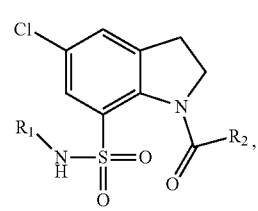

(IIIA")

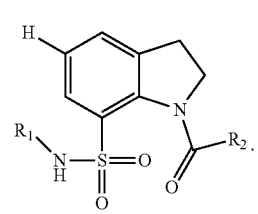

(IIIA''')

In embodiments wherein a compound of Formula (IIIA) includes a compound of Formula (IIIA'), (IIIA"), or (IIIA'''), $R_1$ can be selected from the group consisting of H, $C_{1-8}$alkyl, $C_{1-6}$alkyleneR$_6$, $(C=O)C_{1-6}$alkyl, aryl, and heteroaryl. For example, $R_1$ can be selected from the group consisting of H, methyl, ethyl, n-propyl, isopropyl n-butyl, isobutyl, tert-butyl, n-pentyl, isopentyl, $CH_2$-phenyl, and pyridine.

In some exemplary embodiments, the compound of Formula IIIA can be selected from the group consisting of:

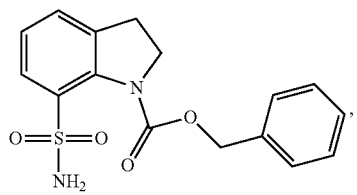

-continued

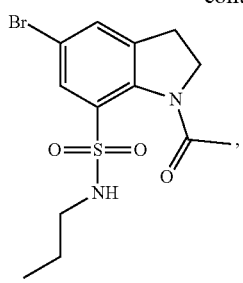

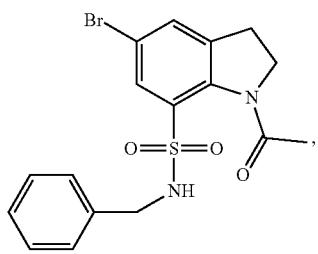

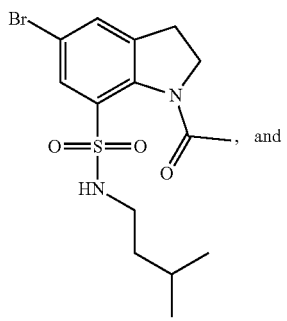, and

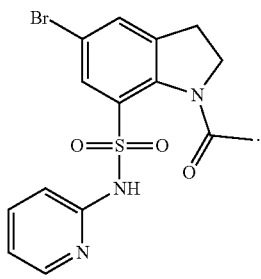

In some cases, the compound of Formula (III) comprises a 6-sulfonamido group and has a structure of Formula (IIIB):

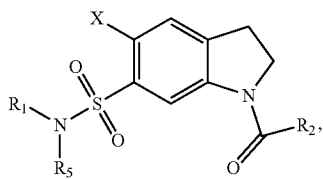

(IIIB)

wherein the substituents are as previously described herein. For example, in some embodiments, X is Br, and in other embodiments, X is Cl. In some exemplary cases X is Br, R₂ is CH₃, and R₅ is H, as shown below in Formula (IIIB'), below. In other cases, X is Cl, R₂ is CH₃, and R₅ is H, as shown below in Formula (IIIB"), below:

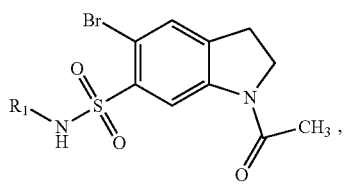

(IIIB')

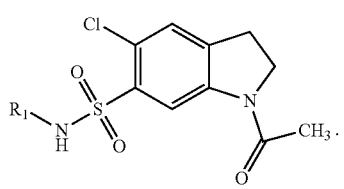

(IIIB")

In some exemplary embodiments, the compound of Formula IIIB can be selected from the group consisting of:

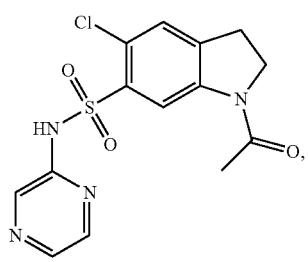

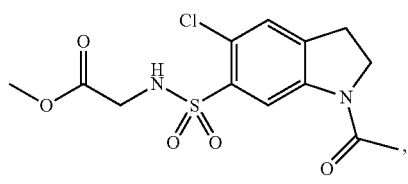

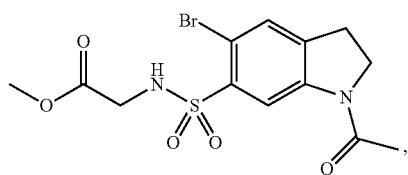

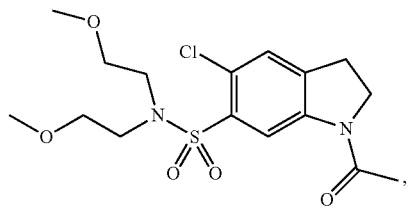

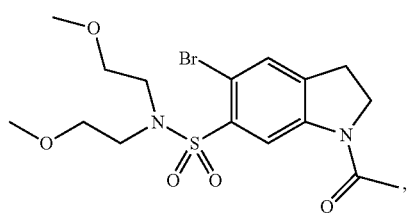

31
-continued
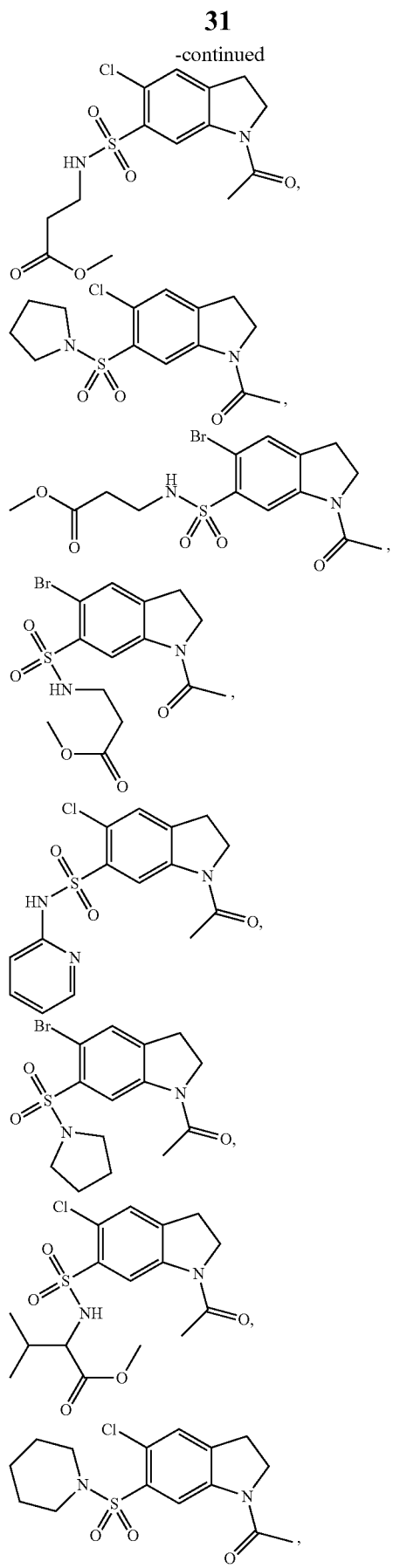
32
-continued
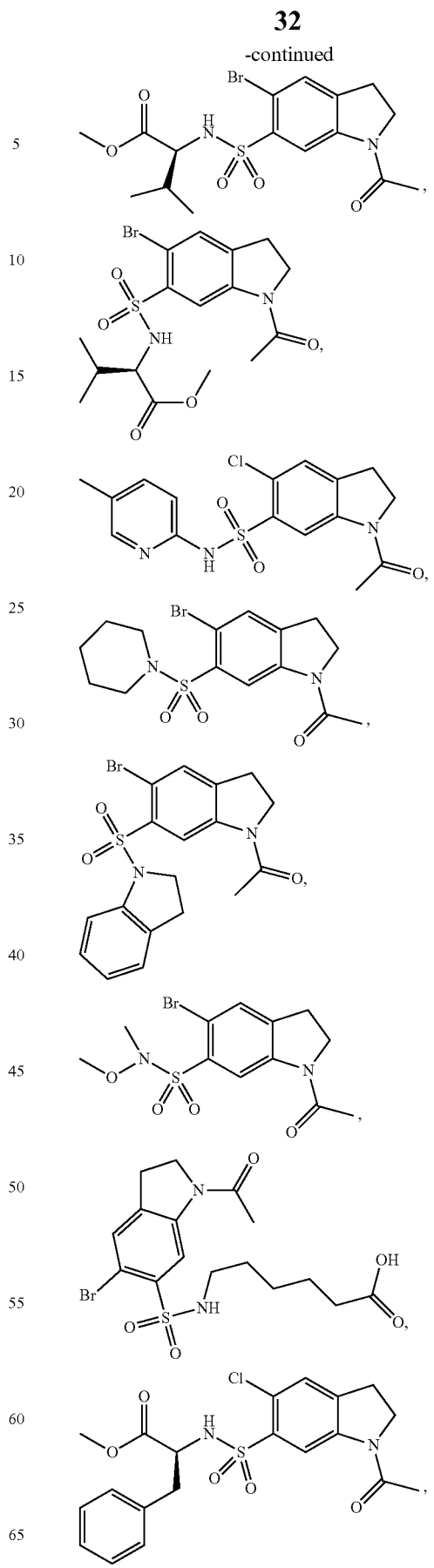

33
-continued
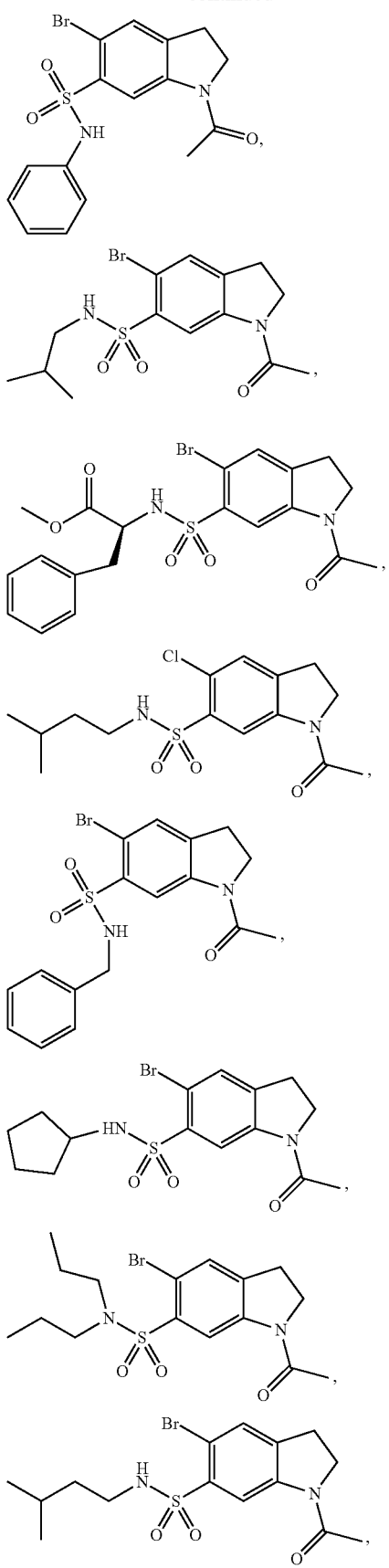
34
-continued
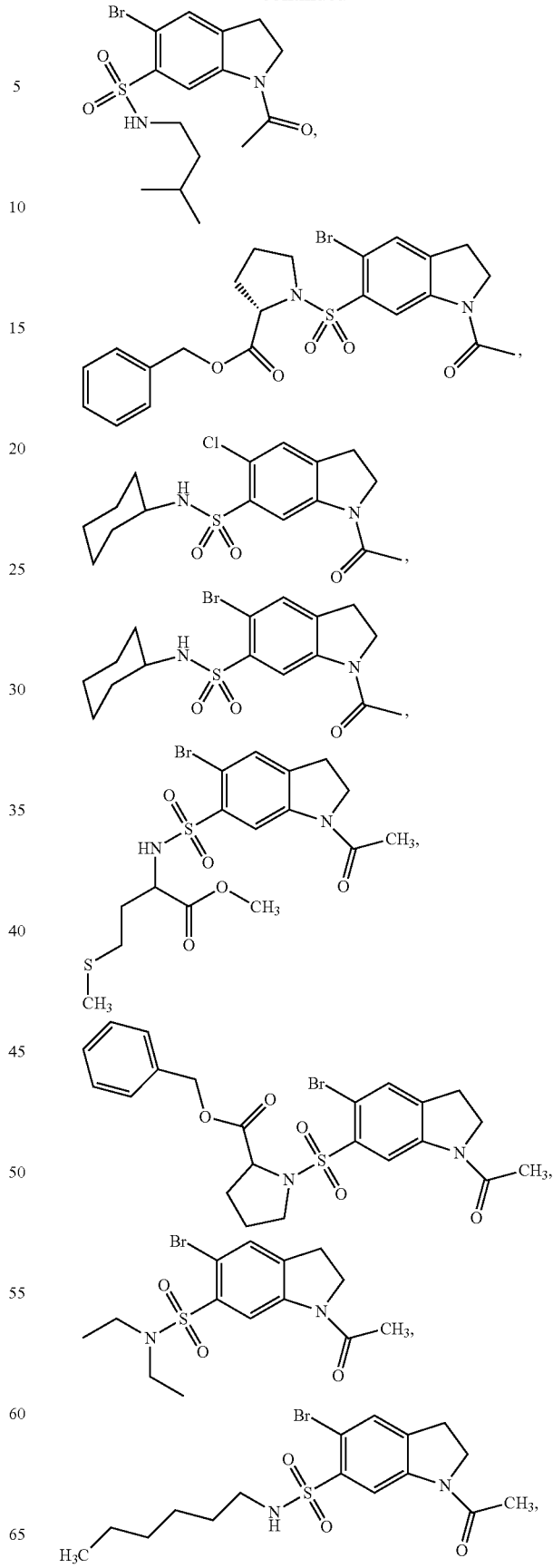

-continued
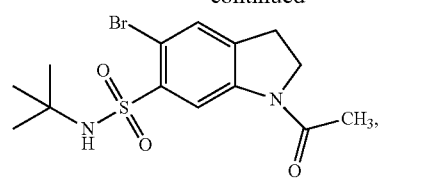
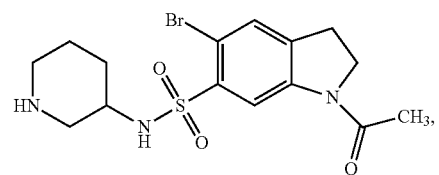
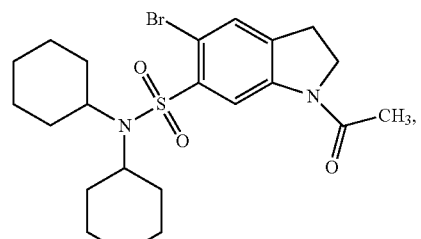
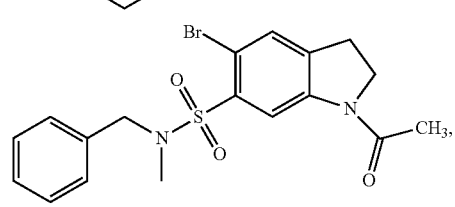
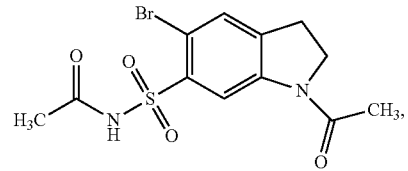
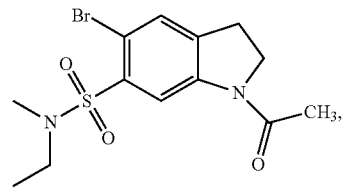
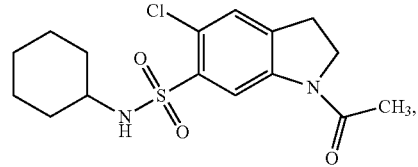
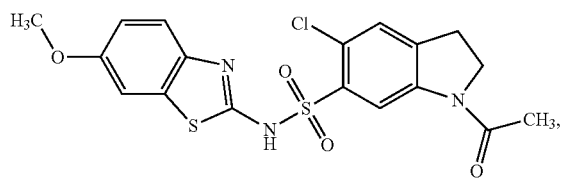
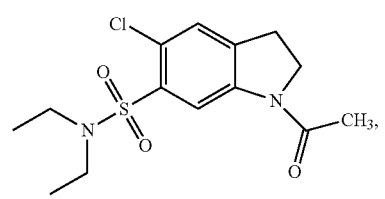
-continued
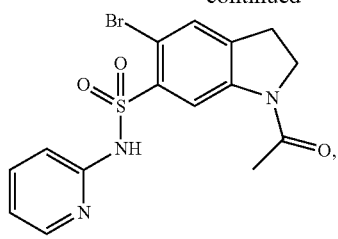
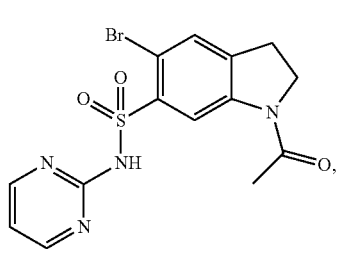
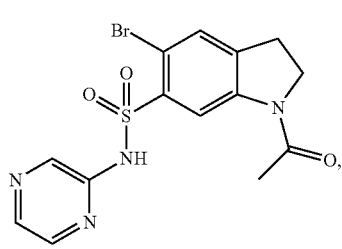
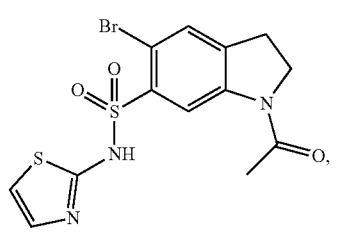
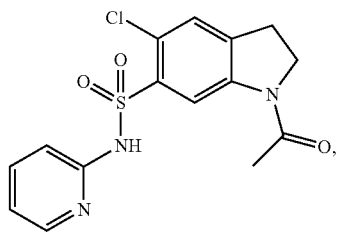
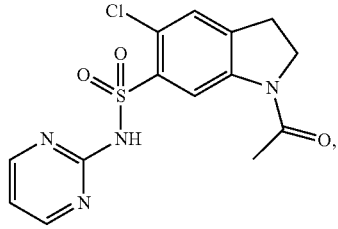
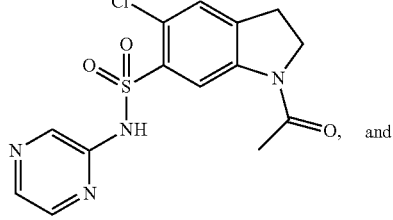, and

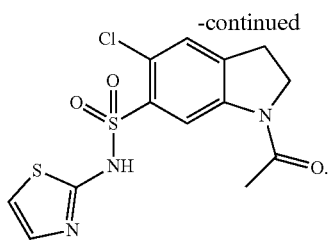

Additionally, salts, hydrates, solvates, and prodrugs of the present compounds also are included in the present invention and can be used in the methods disclosed herein. The present invention further includes all possible stereoisomers and geometric isomers of the compounds of structural Formulae (I), (II), (III), (IIIA), (IIIA'), (IIIA"), (IIIA'''), (IIIB), (IIIB'), or (IIIB"). The present invention includes both racemic compounds and optically active isomers. When a compound of structural Formulae (I), (II), (III), (IIIA), (IIIA'), (IIIA"), (IIIA'''), (IIIB), (IIIB'), or (IIIB") is desired as a single enantiomer, it can be obtained either by resolution of the final product or by stereospecific synthesis from either isomerically pure starting material or use of a chiral auxiliary reagent, for example, see Z. Ma et al., *Tetrahedron: Asymmetry*, 8(6), pages 883-888 (1997). Resolution of the final product, an intermediate, or a starting material can be achieved by any suitable method known in the art. Additionally, in situations where tautomers of the compounds disclosed herein are possible, the present invention is intended to include all tautomeric forms of the compounds.

Compounds of the invention can exist as salts. Pharmaceutically acceptable salts of the compounds of the invention can be used in the methods of the invention. The term "pharmaceutically acceptable salt," as used herein, refers to any salt (e.g., obtained by reaction with an acid or a base) of a compound of the present invention that is physiologically tolerated in the target animal (e.g., a mammal). Salts of the compounds of the present invention may be derived from inorganic or organic acids and bases. The term "pharmaceutically acceptable salts" also refers to zwitterionic forms of the compounds of structural formula (I). Salts of compounds of formula (I) can be prepared during the final isolation and purification of the compounds or separately by reacting the compound with an acid having a suitable cation. The pharmaceutically acceptable salts of compounds of structural formula (I) can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts of compounds of the invention include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, and p-toluenesulfonate salts. Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like. In addition, available amino groups present in the compounds of the invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides.

Synthesis of DapE and NDM-1 Inhibitors

The inhibitors described herein can be synthesized by any method known in the art. For example, the 6-substituted analogs can be prepared according to Scheme 1, below.

Scheme 1. Generic Synthesis of 6-Sulfonamido Indoline Compounds

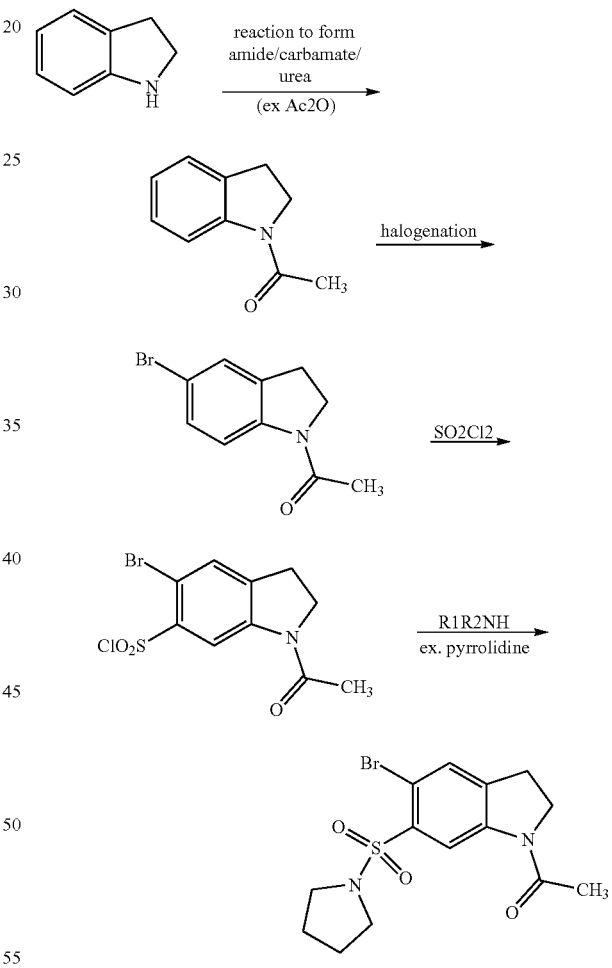

In general, indoline undergoes N-acetylation, and the resulting product is halogenated (e.g., brominated) at the 5-position to form a sole halogenated regioisomer. The regioisomer is then sulfonated in a neat reaction using chlorosulfonic acid to form chlorosulfonyl indoline. The chlorosulfonyl indoline then undergoes a condensation reaction with an amine or amino acid methyl ester to produce the final N-acetyl-5-halo-6-sulfonamide indoline analogs.

The 7-substituted analogs can be prepared according to Scheme 2, below, using intramolecular cyclization.

Scheme 2. Generic Synthesis of 7-Sulfonamido Indoline Compounds

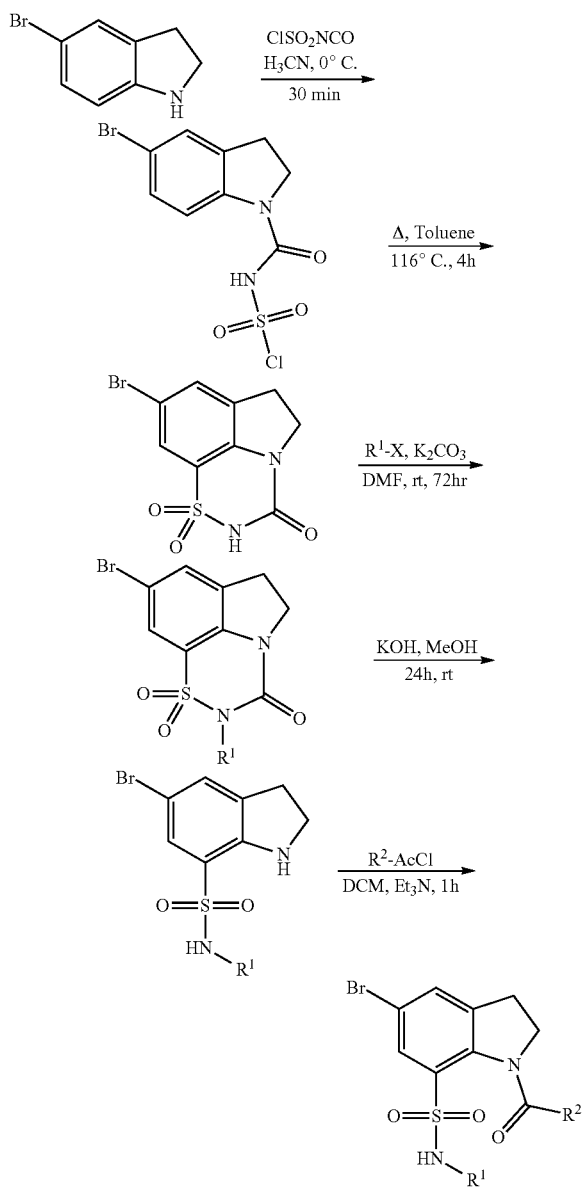

In general, the nitrogen atom of a 5-halo-substituted indoline compound undergoes a condensation reaction with chlorosulfonyl isocyanate, and subsequently undergoes an intramolecular cyclization at the 7-position under Friedel-Crafts conditions to result in a cyclic sulfonurea indoline compound. The resulting compound is subjected to hydrolysis to yield a 7-sulfonamide indoline compound, which is subsequently N-alkylated, as previously described in Scheme 1, to produce the desired 7-sulfonamide indoline compounds.

Additional synthetic procedures for preparing the inhibitors disclosed herein can be found in the Examples section.

Methods

The compounds of structural Formulae (I), (II), (III), (IIIA), (IIIA'), (IIIA"), (IIIA'"), (IIIB), (IIIB') or (IIIB") inhibit DapE and/or MBLs, such as NDM-1, IMP-1, and VIM-2, and are useful in the treatment of a variety of diseases and conditions. In particular, the compounds disclosed herein are used in methods of treating a disease or condition wherein inhibition of DapE and/or a MBL, such as NDM-1, provides a benefit, for example, a bacterial infection.

The methods comprise administering a therapeutically effective amount of a compound of structural Formulae (I), (II), (III), (IIIA), (IIIA'), (IIIA"), (IIIA'"), (IIIB), (IIIB') or (IIIB") to an individual in need thereof. The present methods also encompass administering a second therapeutic agent to the individual in addition to the compound of structural Formulae (I), (II), (III), (IIIA), (IIIA'), (IIIA"), (IIIA'"), (IIIB), (IIIB') or (IIIB"). The second therapeutic agent is selected from drugs known as useful in treating the disease or condition afflicting the individual in need thereof, e.g., an antibiotic known as useful in treating a particular bacterial infection. In some particular embodiments, the compounds disclosed herein are administered with a β-lactam antibiotic drug. Co-administration of the compounds disclosed herein with a β-lactam antibiotic drug maintains and/or enhances the effectiveness of the β-lactam antibiotic drug by preventing destruction of the β-lactam antibiotic drug by MBLs, such as NDM-1, IMP-1, and VIM-2.

Thus, one aspect of the disclosure relates to a method of inhibiting DapE comprising contacting DapE with a compound of Formulae (I), (II), (III), (IIIA), (IIIA'), (IIIA"), (IIIA'"), (IIIB), (IIIB') or (IIIB") in an amount effective to inhibit DapE. For example, DapE can be inhibited in a cell by contacting the cell with a compound of Formulae (I), (II), (III), (IIIA), (IIIA'), (IIIA"), (IIIA'"), (IIIB), (IIIB') or (IIIB"). The contacting of the cell can occur in vitro or in vivo. In some cases, contacting of the cell occurs in vitro. In other cases, contacting of the cell occurs in vivo. The compounds disclosed herein can contact a cell in vivo by administering the compound to a subject in need of DapE inhibition. Therefore, the disclosure includes administering one or more compounds of Formulae (I), (II), (III), (IIIA), (IIIA'), (IIIA"), (IIIA'"), (IIIB), (IIIB') or (IIIB") described herein to a subject, such as a human, in need thereof. In some embodiments, the subject suffers from a bacterial infection.

Another aspect of the disclosure relates to a method of inhibiting MBLs, such as NDM-1, IMP-1, and VIM-2, comprising contacting the MBL (e.g., NDM-1, IMP-1, and/or VIM-2) with a compound of Formulae (I), (II), (III), (IIIA), (IIIA'), (IIIA"), (IIIA'"), (IIIB), (IIIB') or (IIIB") in an amount effective to inhibit the MBL. For example, a MBL (e.g., NDM-1) can be inhibited in a cell by contacting the cell with a compound of Formulae (I), (II), (III), (IIIA), (IIIA'), (IIIA"), (IIIA'"), (IIIB), (IIIB') or (IIIB"). The contacting of the cell can occur in vitro or in vivo. In some cases, contacting of the cell occurs in vitro. In other cases, contacting of the cell occurs in vivo. The compounds disclosed herein can contact a cell in vivo by administering the compound to a subject in need of MBL (e.g., NDM-1) inhibition. Therefore, the disclosure includes administering one or more compounds of Formulae (I), (II), (III), (IIIA), (IIIA'), (IIIA"), (IIIA'"), (IIIB), (IIIB') or (IIIB") described herein to a subject, such as a human, in need thereof. In some embodiments, the subject suffers from a bacterial infection.

Further guidance for using compounds of Formulae (I), (II), (III), (IIIA), (IIIA'), (IIIA"), (IIIA'"), (IIIB), (IIIB') or (IIIB") for inhibiting DapE and/or MBL can be found in the Examples section, below.

Administration of the Inhibitors

The methods disclosed herein can be accomplished by administering a compound of structural Formulae (I), (II), (III), (IIIA), (IIIA'), (IIIA"), (IIIA'"), (IIIB), (IIIB') or (IIIB") as the neat compound or as a pharmaceutical composition.

Administration of a pharmaceutical composition, or neat compound, can be performed during or after the onset of the disease or condition of interest. Typically, the pharmaceutical compositions are sterile, and contain no toxic, carcinogenic, or mutagenic compounds that would cause an adverse reaction when administered. Further provided are kits comprising the compounds disclosed herein and, optionally, a second therapeutic agent useful in the treatment of diseases and conditions wherein inhibition of DapE and/or MBL provides a benefit, packaged separately or together, and an insert having instructions for using these active agents.

In many embodiments, the compounds disclosed herein are administered in conjunction with a second therapeutic agent useful in the treatment of a disease or condition wherein inhibition of DapE and/or MBL (e.g., NDM-1) provides a benefit (e.g., β-lactam antibiotic drug). The second therapeutic agent is different from the compounds disclosed herein, and can be small molecules or macromolecules, such as a proteins, antibodies, peptibodies, DNA, RNA, or fragments of such macromolecules.

The second therapeutic agent is administered in an amount to provide its desired therapeutic effect. The effective dosage range for each second therapeutic agent is known in the art, and the second therapeutic agent is administered to an individual in need thereof within such established ranges.

In the present method, a therapeutically effective amount of one or more of a compound disclosed herein, typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

Thus, also provided herein are pharmaceutical formulations that include a compound of Formulae (I), (II), (III), (IIIA), (IIIA'), (IIIA"), (IIIA'''), (IIIB), (IIIB') or (IIIB"), or a pharmaceutically acceptable salt, as previously described herein, and one or more pharmaceutically acceptable excipients.

The compounds disclosed herein and other pharmaceutically active compounds, if desired, can be administered to a patient or subject by any suitable route, e.g. orally, rectally, parenterally, (for example, intravenously, intramuscularly, or subcutaneously) intracisternally, intravaginally, intraperitoneally, intravesically, or as a buccal, inhalation, or nasal spray. The administration can be to provide a systemic effect (e.g. eneteral or parenteral). All methods that can be used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents. Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. The solid dosage forms may also contain opacifying agents. Further, the solid dosage forms may be embedding compositions, such that they release the active compound or compounds in a certain part of the intestinal tract in a delayed manner. Examples of embedding compositions that can be used are polymeric substances and waxes. The active compound can also be in micro-encapsulated form, optionally with one or more excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferably suppositories, which can be prepared by mixing the compounds of the disclosure with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Pharmaceutical compositions include those wherein a compound disclosed herein is administered in an effective amount to achieve its intended purpose. The exact formulation, route of administration, and dosage is determined by an individual physician in view of the diagnosed condition or disease. Dosage amount and interval can be adjusted individually to provide levels of a compound disclosed herein that is sufficient to maintain therapeutic effects.

Toxicity and therapeutic efficacy of the compounds disclosed herein can be determined by standard pharmaceutical procedures in cell cultures or experimental animals, e.g., for determining the maximum tolerated dose (MTD) of a compound, which defines as the highest dose that causes no toxicity in animals. The dose ratio between the maximum tolerated dose and therapeutic effects (e.g. inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a compound disclosed herein required for use in therapy varies with the nature of the condition being treated, the length of time that activity is desired, and the age and the condition of the patient, and ultimately is determined by the attendant physician. Dosage amounts and intervals can be adjusted individually to provide plasma levels of the inhibitors that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a present IAP protein inhibitor can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

A compound of structural formula (I) used in a method of the present invention can be administered in an amount of about 0.005 to about 500 milligrams per dose, about 0.05 to about 250 milligrams per dose, or about 0.5 to about 100 milligrams per dose. For example, a compound disclosed herein can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

The dosage of a composition containing a compound disclosed herein, or a composition containing the same, can be from about 1 ng/kg to about 200 mg/kg, about 1 μg/kg to about 100 mg/kg, or about 1 mg/kg to about 50 mg/kg. The dosage of a composition can be at any dosage including, but not limited to, about 1 μg/kg. The dosage of a composition may be at any dosage including, but not limited to, about 1 μg/kg, 10 μg/kg, 25 μg/kg, 50 μg/kg, 75 μg/kg, 100 μg/kg, 125 μg/kg, 150 μg/kg, 175 μg/kg, 200 μg/kg, 225 μg/kg, 250 μg/kg, 275 μg/kg, 300 μg/kg, 325 μg/kg, 350 μg/kg, 375 μg/kg, 400 μg/kg, 425 μg/kg, 450 μg/kg, 475 μg/kg, 500 μg/kg, 525 μg/kg, 550 μg/kg, 575 μg/kg, 600 μg/kg, 625 μg/kg, 650 μg/kg, 675 μg/kg, 700 μg/kg, 725 μg/kg, 750 μg/kg, 775 μg/kg, 800 μg/kg, 825 μg/kg, 850 μg/kg, 875 μg/kg, 900 μg/kg, 925 μg/kg, 950 μg/kg, 975 μg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, or 200 mg/kg. The above dosages are exemplary of the average case, but there can be individual instances in which higher or lower dosages are merited, and such are within the scope of this invention. In practice, the physician determines the actual dosing regimen that is most suitable for an individual patient, which can vary with the age, weight, and response of the particular patient.

When a patient or subject is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered via a tablet, while another is administered via injection or orally as a syrup. All combinations, delivery methods and administration sequences are contemplated.

In jurisdictions that forbid the patenting of methods that are practiced on the human body, the meaning of "administering" of a composition to a human subject shall be restricted to prescribing a controlled substance that a human subject will self-administer by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

EXAMPLES

The following examples are provided for illustration and are not intended to limit the scope of the invention Example 1. Preparation 1-Acetyl 5-bromo 6-Substituted Sulfonamide Indolines

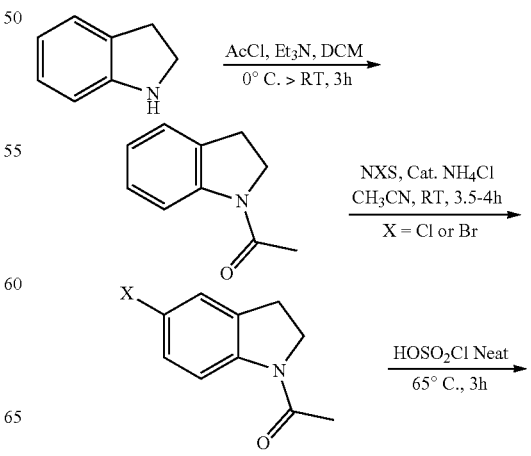

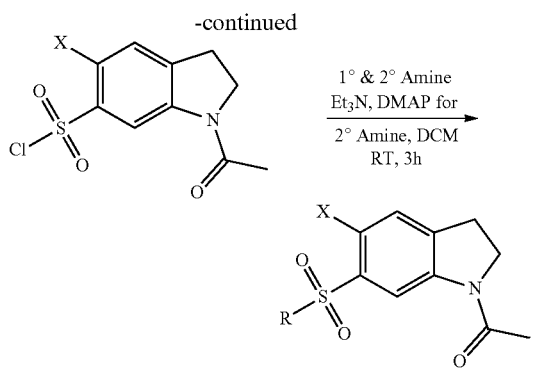

To a solution of indoline (1, 20.0 g, 0.168 mol) dissolved in dichloromethane (193 mL) was added triethylamine (82 mL) via pouring and with stirring in air for 10 min at room temperature. Another solution of acetyl chloride (17.4 g, 0.222 mol) in dichloromethane (129 mL) was added to the first solution slowly via pipet and maintained at 5° C. for 15 minutes. The resulting solution was stirred 18 hours at room temperature and checked for completion by TLC with a mobile phase of 50% ethyl acetate/hexanes. The solution was diluted with deionized water and extracted with dichloromethane three times. The organic portion was washed once with deionized water, once with 1N HCl, twice with deionized water, and once with brine. The organic portion was then dried over $Na_2SO_4$ for 15 minutes. After drying, the resulting solution was concentrated by rotary evaporation to yield the desired N-acetyl indoline (2) as a light brown/orange solid (25.2 g, 93.2%).

To a solution of 2 (2.00 g, 12.4 mmol) in glacial acetic acid (13 mL) was added liquid bromine (0.61 mL) dropwise while stirring. The solution turned from dark brown to orange/yellow upon stirring. After thirty minutes (or when finished as determined by TLC), the reaction was quenched by pouring it into water with stirring. A gold colored solid remained. The heterogeneous mixture was filtered through a Büchner funnel and dried via high vacuum to obtain the desired mono 5-bromo substituted N-acetyl indoline as a light brown solid (94% yield).

In the case of 5-chloro substitution, the 5-chloro indoline compound was synthesized by slowly adding purified N-chlorosuccinimide (NCS) (1.74 g, 13.03 mmol) to a solution of 2 (2.00 g, 12.4 mmol) and a catalytic amount of $NH_4OAc$ (96.1 mg, 10 mol %) in acetonitrile (65 mL) and monitored by TLC until completion. The NCS was purified through recrystallization in glacial acetic acid (10.0 grams in 50.0 mL), filtered and washed with hexane and then dried under vacuum to form 3.

Chlorosulfonic acid (18.75 mL) was slowly added to 3 (2.50 g, 10.41 mmol) with stirring and a temperature between 60° and 70° C. for 3 hr. The resulting black homogenous solution was allowed to cool to room temperature, and then poured slowly over ice with stirring. A precipitate was formed (off-white for the 5-bromo analogs, and light yellow/gold for the 5-chloro analogs), filtered via vacuum filtration, washed with deionized water, and dried in vacuum to produce 4. The N-acetyl 5-chloro 6-chlorosulfonyl indoline compounds (49% yield) were yellow-gold solids. The N-acetyl 5-bromo 6-chlorosulfonyl indoline compounds (52% yield) were powdery, white solids.

Compound 4 (50 mg, 0.148 mmol) was reacted with the desired amine (0.185 mmol) and triethylamine (31.0 μL) in dichloromethane with stirring for one hour, after which the reaction was diluted with dichloromethane. The organic layer was washed one time with deionized water, twice with 1M HCl, once with 1M NaCl dried over sodium sulfate, filtered, and concentrated on the rotary evaporator to produce the 1-acetyl 5-bromo 6-substituted sulfonamide indolines products as solids ranging in colors from of white to pale yellow to light brown to dark brown depending on the sulfonamide derivative (82% average yield).

This above procedure was carried out with different primary amines yielding reaction times of 1-4 hours. Secondary amines followed the same synthesis except for the addition of 4-dimethylamino pyridine (DMAP) (10 mol %) catalyst in the last step of the synthesis, resulting in an average reaction time between 4 and 24 hours. For nitrogen-containing heterocycles, primary amines with a DMAP catalyst also was used with a reaction time from 4 hours to 24 hours. Addition of 1M HCl to these compounds created a "polymer like layer" between the aqueous and organic layer. The aqueous layer was extracted 2 times with dichloromethane and combined with the original organic layer. The mixture was concentrated and dried via high vacuum overnight.

Example 2. Synthesis of 7-Sulfonamide Indolines by Intramolecular Cyclization Under Friedel-Crafts Conditions

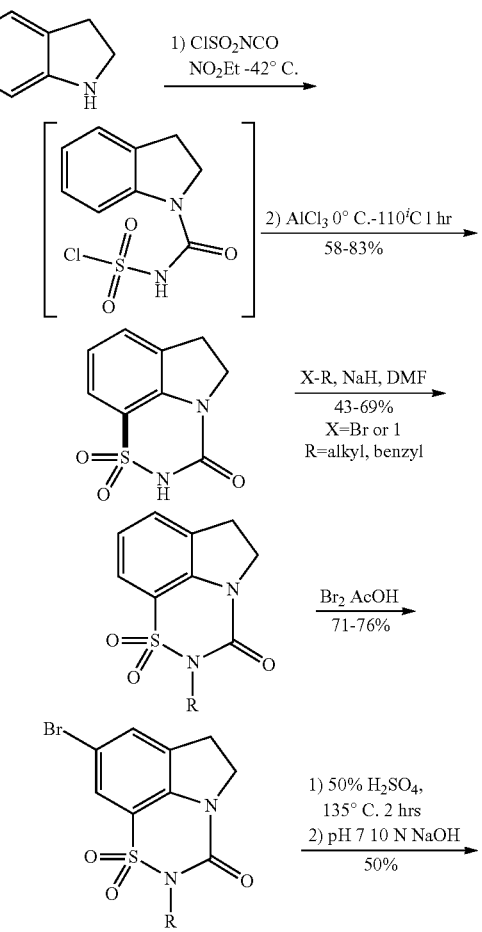

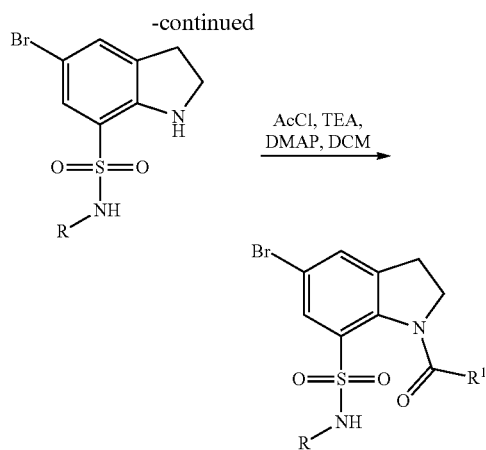

TEA = Triethylamine
DMAP = N,N-dimethyl aminopyridine

Indoline was slowly added dropwise with stirring to a solution of chlorosulfonyl isocyanate (1.80 mL, 18.4 mmol) in nitroethane (32 mL) that had been cooled to −42° C. The intermediate precipitated, the solution became cloudy and white, and the mixture was slowly warmed to room temperature over one hour with continued stirring. Aluminum chloride (2.45 g, 18.4 mmol) was added to the solution in one portion and allowed to stir for 15 minutes at room temperature. The solution went from cloudy and white to clear, pale yellow, to a light purple, and then to a dark purple over this time period. The reaction was then heated to 110° C. for one hour. The mixture was cooled to room temperature and quenched by pouring into ice water slowly where a black precipitate formed. The solid was isolated by filtering via vacuum filtration. A dark gray clay-like substance was obtained and dried overnight via vacuum yielding the cyclic sulfonurea indoline (58-83%) as a dark gray solid compound. The solid was not purified and taken into the next reaction.

NaH in 60% mineral oil (30 mg) was added to a solution of cyclic sulfonurea indoline (150 mg, 0.67 mmol) in DMF (2 mL), and the resulting mixture was allowed to stir. The appropriate halogen alkylating agent (0.78 mmol) was added to the solution dropwise and allowed to stir until reaction completion, as determined by TLC. The reaction was diluted with ethyl acetate, washed with 0.1 M HCl, washed with saturated NaHCO$_3$, and then washed with brine. The organic portion was concentrated in vacuum to yield the solid alkylation product (43%-69%).

The alkylated cyclic sulfonurea indolines were dissolved in a minimum amount of glacial acetic acid and stirred vigorously. Bromine was slowly added, dropwise with stirring, to this solution that was cooled in an ice bath. The reaction was warmed to room temperature, left to stir for 75 minutes, and then heated to 50° C. for 1 hour. Reactions were quenched by pouring the reaction solutions onto ice water, isolating the white solids via vacuum filtration, and drying the products via high vacuum to produce light brown solids (71%-76.3% yield).

A solution of the 5-bromo cyclic sulfonureas in 50% sulfuric acid was heated to 135° C. for two hours. The reaction was cooled to room temperature and then neutralized carefully with a 10 N NaOH solution over ice. The aqueous layer was extracted with ethyl acetate three times, the organic fractions were combined and dried over magnesium sulfate, and then the solution was concentrated in vacuum to yield light yellow solids (50%).

Triethylamine was added to a solution of 5-bromo 7-sulfonamide indolines in dichloromethane, and the solution was stirred at room temperature for 15 minutes. The mixture was cooled to 0° C. via ice bath where acetyl chloride was slowly added dropwise, maintaining the temperature between 0-10° C. After complete addition, the reaction was warmed to room temperature and stirred until complete, as determined by TLC. The reaction was diluted with dichloromethane and washed one time with dilute HCl, one time with water, and then once with brine. The organic layer was dried over Na$_2$SO$_4$ and concentrated in vacuum producing the final N-acetyl 5-Br 7-sulfonamide indoline analogs.

Example 3. Synthesis of N-Acyl-7-Sulfonamide Indolines

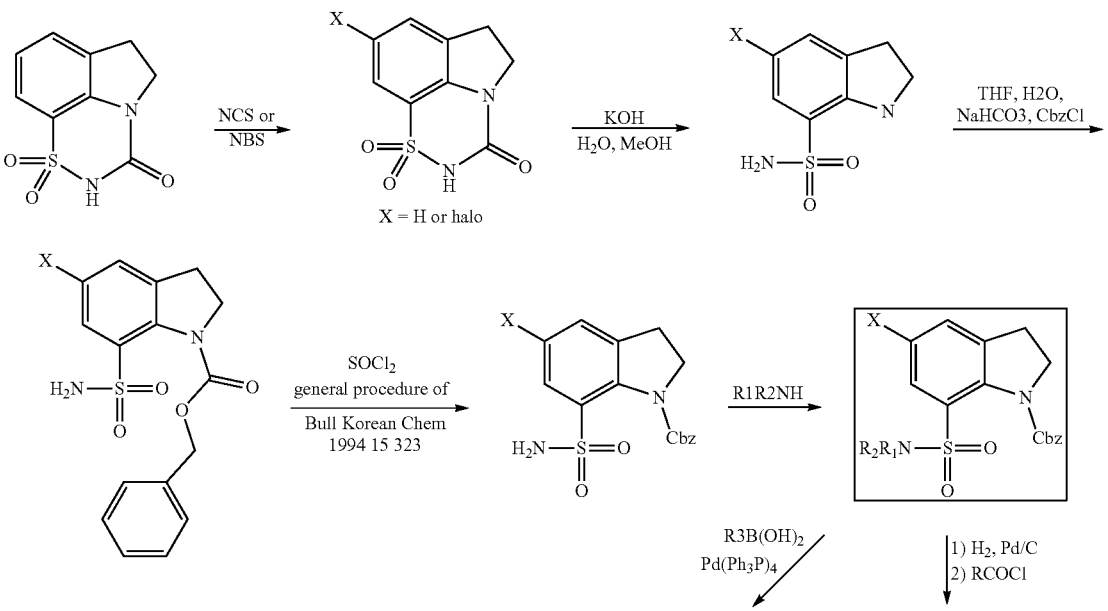

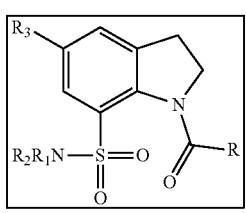 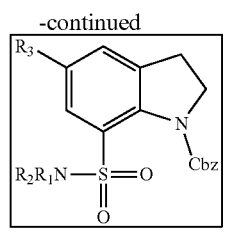 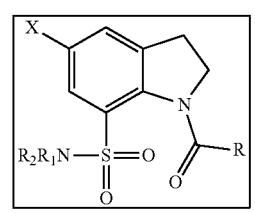

The cyclic sulfourea indoline can be prepared by methods previously disclosed herein. In this scheme, the cyclic sulfonurea indoline is hydrolyzed before alkylation producing a primary 7-sulfonamide indoline. After hydrolysis the indoline is acetylated, as previously described herein, followed by bromination.

Example 4. Synthesis of 7-Sulfonamide Indolines by 0-Directed Borylation Followed by Pd(0) Catalyzed Chlorsulfonylation Synthesis of 7-Sulfonamide Indoline by O-Directed Borylation and Pd Catalyzed Cholorosulfonylation

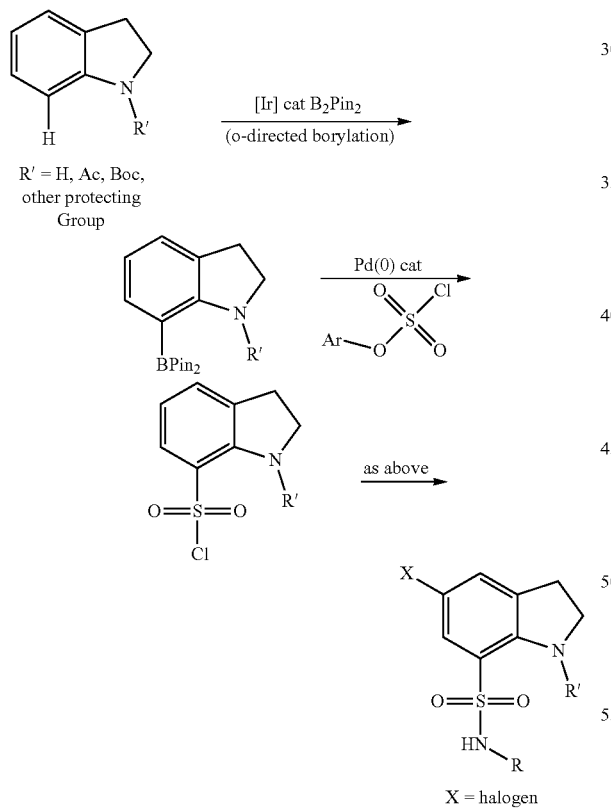

Indoline, with or without a carbonyl containing N-protecting group, was borylated ($B_2Pin_2$) at the 7-position using an ortho-directing iridium catalyst, such as $[Ir(Ome)COD]_2$ or $[Ir(COD)Cl]_2$ catalyst in a glove box under a nitrogen atmosphere. Nucleophilic displacement of the Bpin group using a Pd(0) catalyst and an aryl sulfanate group produced the 7-chlorsulfonyl indoline. The chlorsulfonyl indoline can react with desired amines, as previously described herein, to produce the 7-sulfonamide indolines.

Example 5. Synthesis of 7-Sulfonamide Indolines by Ortho-Directed Lithiation and Sulfur Trioxide C—Li Insertion Synthesis of 7-Sulfonamide Indolines by O-Directed Lithiation and Sulfurtrioxide C—Li Insertion

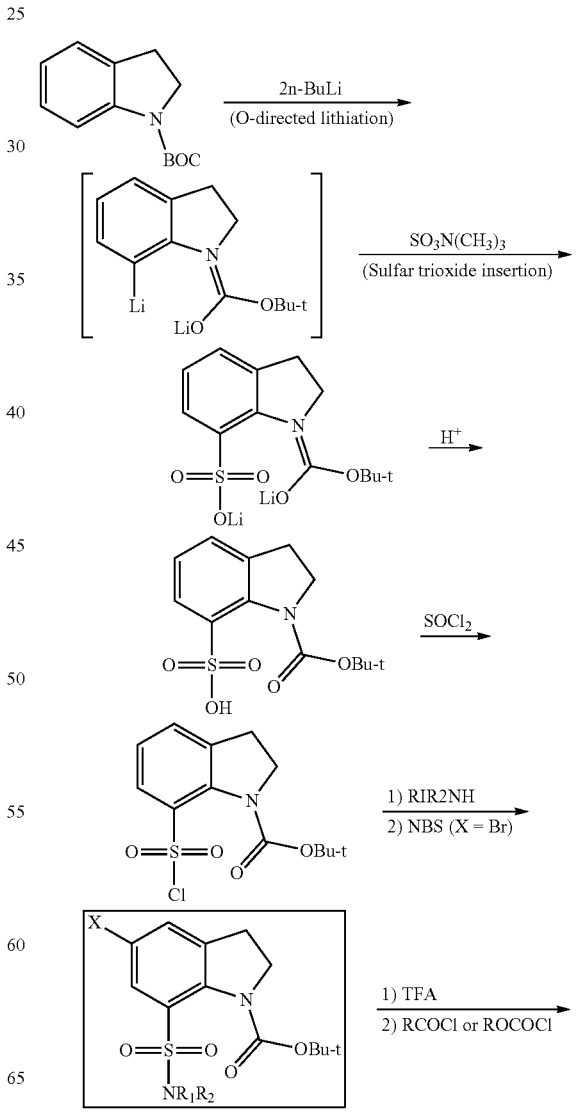

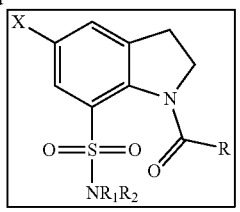

Indoline was protected at the nitrogen with a BOC group by slowly adding di-tert-butyl dicarbonate into a solution of indoline in THF. The resulting solution was stirred at room temperature in an atmosphere of nitrogen for 24 hours, or until done as determined but TLC. After an aqueous workup, a dark brown oil was obtained. This N-Boc indoline was dissolved in THF or ether, with or without TMEDA, and then was reacted with n-BuLi by slow addition at either room temperature, 0° C., or −78° C. The reaction was allowed to stir between 30 minutes and 24 hours to provide the dilithium salt on the 7-position and the carbonyl group. This solution was slowly added over time and under nitrogen to a second solution composed of a sulfur trioxide trimethyl amine. The resulting solution was allowed to stir for 24 hours, and then was subjected to an aqueous work up (KOH, extraction with ethyl acetate, washing with HCl). The reaction mixture was then stripped down and washed with ether to result in a white precipitate, which was then washed again with ether. Organic fractions were combined and the solvent was removed to produce a dark brown sticky solid. The resulting 7-sulfonic acid indoline was brominated under standard conditions listed previously to produce a light brown powdery solid. This brominated sulfonic acid product can be reacted with thionyl chloride to produce the 7-sulfonyl chloride indoline under standard methods. Reactions with desired amines as described in previous syntheses will produce N-Boc 5-Bromo 7-sulfonamide indolines.

Example 6. Synthesis of N-Acetylindoline

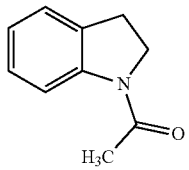

To a RBF was added 0.850 ml (8.42 mmol, 1 eq.) indoline (1) into 9 ml of DCM and stirred over an ice bath for 5 minutes. Then 3.87 mL of TEA was added and the reaction was left to stir for 5 m after which 0.852 ml of acetyl chloride was added to the stirred reaction mixture over 5 minutes then left to stir for 2 h. The reaction mixture was quenched with 15 ml of water and extracted 3× with DCM to yield a brown tar. The crude product was then purified through flash column using 50-49-1 Ea-Petroleum Ether-AcOH solvent system as eluent to yield the desired product. Product collected (1.10 g, 80%) as an orange solid: mp 96-99° C.; 1H NMR (500 MHz, CDCl3) δ 2.22 (s, 3H), 3.20 (t, J=6.8 Hz, 2H), 4.05 (t, J=6.8 Hz, 2H), 7.00 (d, J=6.0 Hz, 1H), 7.03-7.18 (m, 2H), 8.20 (d, J=6.4 Hz, 1H); 13C NMR (125 MHz, CDCl3) δ 24.4, 28.1, 48.9, 117.1, 123.7, 124.6, 127.7, 131.2, 143.0, 168.9; MS ESI m/z 184 ([M+Na]+, 100); HRMS EI (DFA) m/z calcd. for C10H11NO [M+] 161.0841, found 161.0840. See Shalygina et al., Izv. Vyssh. Uchebn. Zaved., Khim. Khim. Tekhnol. 2004, 47, 91-961; Wu et al., Bioorg. Med. Chem. Lett. 2004, 14, 4533-4537.

Example 7. General Procedure for Halogenations of N-Acetylindoline at the 5-Position (3a, 3b)

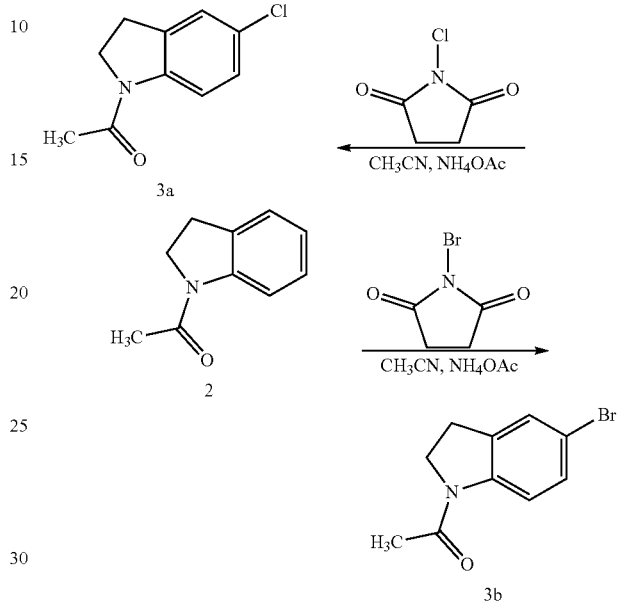

A mixture of 1-acetylindoline (2.01 g, 12.469 mmol) and NCS (1.748 g, 13.092 mmol) or NBS (2.330 g, 13.092 mmol) in 60 mL of acetonitrile was left to stir at room temperature for 3.5 h. After the solvent was removed under vacuum, the residue was diluted with water, extracted 3× with DCM, and concentrated to dryness. The collected crude product was then purified by flash chromatography on silica gel eluting with 1:1 EtOAc/hexane. See Hu et al., Bioorg. Med. Chem. 2005, 13, 6629-6644. The product 1-acetyl-5-chloroindoline (3a) was collected as an orange solid (2.02 g, 83%): mp ° C.; 1H NMR (500 MHz, CDCl3) δ 8.13 (d, J=8.5 Hz, 1H), 7.14 (d, J=9.5 Hz, 1H), 7.13 (s, 1H), 4.06 (t, J=8.0 Hz, 2H), 3.17 (t, J=8.5 Hz, 2H), 2.21 (s, 3H). The product 1-acetyl-5-bromoindoline (3b) was collected as a yellow-orange solid (1.81 g, 61%): mp 122-124° C.; 1H NMR (500 MHz, CDCl3) δ 8.05 (d, J=8.5 Hz, 1H), 7.26 (d, J=9.5 Hz, 1H), 7.24 (s, 1H), 4.01 (t, J=8.5 Hz, 1H), 3.14 (t, J=8.5 Hz, 2H), 2.19 (s, 3H).

Example 8. General Procedure for Sulfonation of 5-Halo, N-Acetylindoline at the 6-Position (4a, 4b)

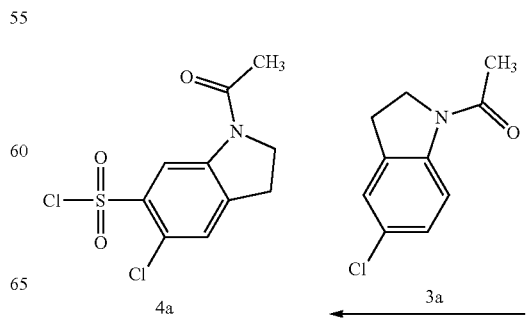

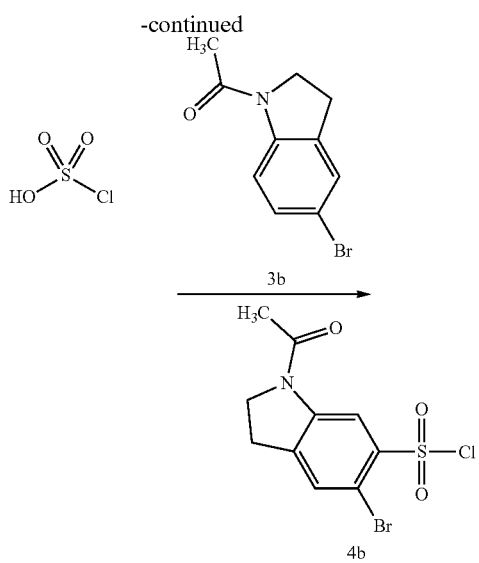

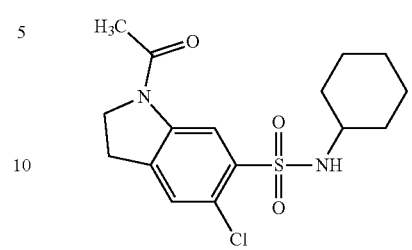

Compound 4a was prepared as follows. About 0.300 g of 1-acetyl-5-chloroindoline was added to chlorosulfonic acid (2.25 ml) in small portions with intensive stirring and cooling using ice. The mixture was heated at 60° C. and stirred for 3.5 h. TLC was taken to confirm reaction completion. The reaction was poured onto ice to result in a grey precipitate, which was filtered off and re-crystallized from methyl ethyl ketone. Yield: 0.3411 g; mp 190° C.; $^1$H NMR (500 MHz, CDCl3) δ 8.98 (s, 1H), 7.42 (s, 1H), 4.02 (t, J=9.0 Hz, 2H), 3.33 (t, J=8.0 Hz, 2H), 2.09 (s, 3H).

Compound 4b was prepared as follows. About 1.199 g of 1-acetyl-5-bromoindoline was added to chlorosulfonic acid (8.5 ml) in small portions with intensive stirring and cooling using ice. The mixture was heated at 60° C. stirred for 3 h. TLC was taken to confirm reaction completion. The reaction was poured onto ice to result in a white precipitate, which was filtered off and re-crystallized from methyl ethyl ketone. Yield: 1.690 g; mp 212° C.; $^1$H NMR (300 MHz, CDCl3) δ 9.03 (s, 1H), 7.63 (s, 1H), 4.20 (t, J=8.5 Hz, 2H), 3.12 (t, J=8.0 Hz, 2H), 2.28 (s, 3H). See Ikan et al., *J. Chem. Eng. Data* 1971, 16, 125-126.

Example 9. General Procedure for Preparing Sulfonamide Indolines from 1-Acetyl-5-holoindoline-7-Sulfochloride Either 1-acetyl-5-chlorindoline-7-sulfochloride (0.1 g, 0.340 mmol, 1 eq.) or 1-acetyl-5-bromoindoline-7-sulfochloride (0.1 g, 0.295 mmol, 1 eq.) was added to an 8 g reaction vial along with a stir bar. A 5 mol % amount of DMAP also was added to the vial if the procedure involved reaction of a secondary amine. DCM (3 mL) was then added until all the indoline dissolved, followed by 1.5 eq. of triethylamine. The desired amine (1.25 eq) was then added to the vial and the vial was sealed. The reaction was allowed to stir at room temperature for 2 to 3 hours or until TLC indicated reactions complete. Upon completion, each reaction was diluted with dichloromethane, and then by 1N HCl. The aqueous layers were then extracted three times with dichloromethane to remove the product from the aqueous layer. The fractions were then combined and washed once more with brine, then dried over sodium sulfate and condensed to dryness on the vacuum. The crude product was recrystallized from a ratio of 1 to 2 dichloromethane in EA.

See Shalygina et al., Izv. Vyssh. Uchebn. Zaved., Khim. Khim. Tekhnol. 2004, 47, 91-961.

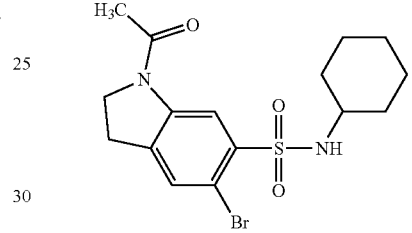

Product collected (0.0953 g, 79%) as a grayish white solid: mp 224-232° C.; $^1$H NMR (300 MHz, CDCl3) δ 8.9 (s, 1H), 7.28 (s, 1H), 4.90 (t, J=6.0 Hz, 1H), 4.14 (t, J=8.7 Hz, 2H), 3.25 (t, J=8.7 Hz, 2H), 2.93 (dd, J=13.7, 7.2 Hz, 2H), 2.24 (s, 3H), 1.36 (dd, J=14.4, 6.9 Hz, 2H), 1.6 (m, 1H), 0.84 (d, J=6.6 Hz, 6H).

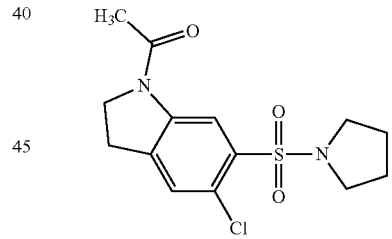

Product collected (0.0926 g, 78%) as a tan solid: mp 226-228° C.; $^1$H NMR (300 MHz, CDCl3) δ 8.911 (s, 1H), 7.465 (s, 1H), 5.55 (d, J=7.5 Hz, 1H), 4.14 (t, J=8.5 Hz, 2H), 3.25 (t, J=9 Hz, 2H), 3.16 (m, 1H), 2.24 (s, 3H), 1.82-1.14 (m, 10H).

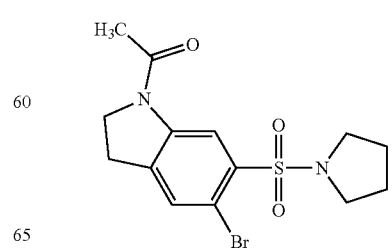

Product collected (0.103 g, 92%) as a yellowish tan solid: mp 197-201° C.; $^1$H NMR (500 MHz, CDCl3) δ 8.67 ( ), 7.27 ( ), 4.13 ( ), 3.44 ( ), 3.24 ( ), 2.23 ( ), 1.96 ( ); 13C NMR (500 MHz, CDCl3) δ 169.3, 142.1, 137.1, 136.4, 128.2, 126.6, 117.4, 49.2, 48.3, 27.9, 26.0, 24.3.

Product collected (0.0988 g, 90%) as a light brown crystalline solid: mp 238-240° C.; $^1$H NMR (500 MHz, CDCl3) δ 8.68 (s, 1H), 7.50 (s, 1H), 4.13 (t, J=9.0 Hz, 2H), 3.46 (t, J=6.5 Hz, 4H), 3.24 (t, J=6.0 Hz, 2H), 2.23 (s, 3H), 1.98 (t, J=7.0 Hz, 2H); $^{13}$C NMR (500 MHz, CDCl3) δ 169.3, 142.9, 138.3, 137.1, 131.7, 118.0, 114.0, 49.2, 48.4, 27.8, 26.0, 24.3. MS ESI m/z 373 [M+H]+.

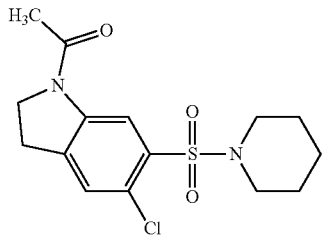

Product collected (0.104 g, 79%) as a tan crystalline solid: ° C.; $^1$H NMR (500 MHz, CDCl3) δ 8.72 (s, 1H), 7.27 (s, 1H), 4.13 (t, J=9.0 Hz, 2H), 3.28 (t, J=66.5 Hz, 4H), 3.24 (t, J=9.0 Hz, 2H), 2.23 (s, 3H), 1.66-1.61 (m, 4H), 1.54 (dd, J=11.0, 6.0 Hz, 2H); $^{13}$C NMR (500 MHz, CDCl3) δ 169.1, 142.1, 137.2, 135.9, 128.1, 126.6, 118.7, 49.1, 47.0, 27.9, 25.8, 24.2, 24.0.

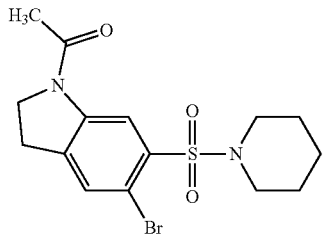 [SMILES: CC(=O)N1CCc2cc(Cl)c(S(=O)(=O)N3CCCCC3)cc21]

Product collected (0.114 g, 70%) as a off white crystalline solid: mp 212-214° C.; $^1$H NMR (500 MHz, CDCl3) δ 8.73 (s, 1H), 7.47 (s, 1H), 4.12 (t, J=8.0 Hz, 2H), 3.29 (t, J=4.5 Hz, 4H), 3.24 (t, J=8.5 Hz, 2H), 2.23 (s, 3H), 1.63 (m, 4H), 1.552 (m, 2H); $^{13}$C NMR (500 MHz, CDCl3) δ 169.3, 142.8, 137.7, 137.4, 131.6, 118.9, 114.0, 49.2, 47.0, 44.8, 27.8, 25.8, 24.3, 24.0.

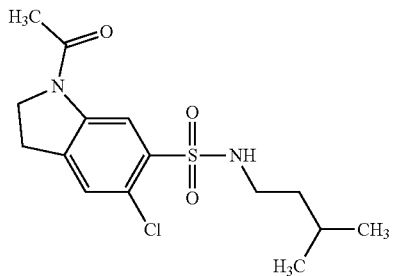 [SMILES: CC(=O)N1CCc2cc(Cl)c(S(=O)(=O)NCCC(C)C)cc21]

Product collected (0.117 g, 99%) as a tan solid: mp 174-180° C.; $^1$H NMR (300 MHz, CDCl3) δ 8.89 (s, 1H), 7.28 (s, 1H), 4.90 (t, J=6.0 Hz, 2H), 4.14 (t, J=8.7 Hz, 2H), 3.25 (t, J=8.7 Hz, 2H), 2.93 (dd, J=13.7, 7.2 Hz, 2H), 2.24 (s, 3H), 1.36 (dd, J=14.4, 6.9 Hz, 2H), 1.60 (m, 1H), 0.84 (d, J=6.6 Hz, 6H).

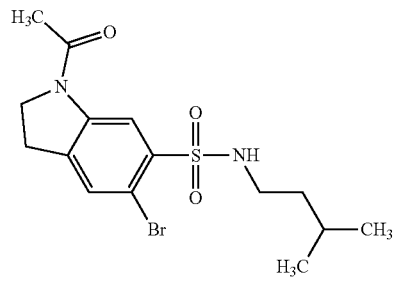 [SMILES: CC(=O)N1CCc2cc(Br)c(S(=O)(=O)NCCC(C)C)cc21]

Product collected (0.114 g, 99%) as a orange tacky solid: mp 190-191° C.; $^1$H NMR (500 MHz, CDCl3) δ 8.88 (s, 1H), 7.48 (s, 1H), 5.04 (bs, 1H), 4.14 (t, J=8.5 Hz, 2H), 3.25 (t, J=9.0 Hz, 2H), 2.92 (t, J=7.5 Hz, 2H), 2.24 (s, 3H), 1.67 (m, 1H), 1.38 (s, 2H), 0.84 (d, J=7.0 Hz, 6H).

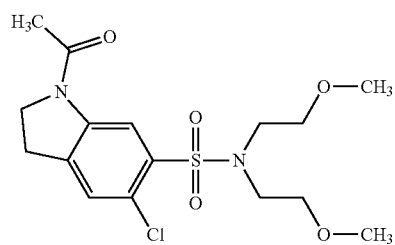 [SMILES: COCCN(CCOC)S(=O)(=O)c1cc2c(cc1Cl)CCN2C(C)=O]

Product collected (0.150 g, 113%) as a grayish tan solid: mp 88-93° C.; $^1$H NMR (500 MHz, CDCl3) δ 8.77 (s, 1H), 7.27 (s, 1H), 4.13 (t, J=8.5 Hz, 2H), 3.59 (t, J=6.0 Hz, 6H), 3.57 (t, J=5.5 Hz, 4H), 3.52 (t, J=5.0 Hz, 4H), 3.29 (s, 6H), 2.23 (s, 3H); $^{13}$C NMR (500 MHz, CDCl3) δ 169.1, 142.2, 1373, 137.2, 127.9, 126.7, 118.7, 71.8, 71.8, 59.4, 59.0, 49.2, 48.7, 47.9, 28.0, 24.3, 8.9.

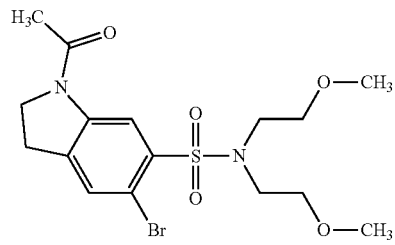 [SMILES: COCCN(CCOC)S(=O)(=O)c1cc2c(cc1Br)CCN2C(C)=O]

Product collected (0.125 g, 97%) as a yellowish tan solid: mp 110-111° C.; $^1$H NMR (500 MHz, CDCl3) δ 8.78 (s, 1H), 7.49 (s, 1H), 4.23 (t, J=8.5 Hz, 2H), 3.40 (t, J=6.0 Hz, 4H), 3.53 (t, J=5.5 Hz, 4H), 330 (s, 6H), 3.24 (t, J=9.0 Hz, 2H), 2.23 (s, 3H); $^{13}$C NMR (500 MHz, CDCl3) δ 169.2, 142.8, 139.0, 137.2, 131.5, 118.7, 114.2, 71.7, 59.0, 48.8, 27.8, 24.3, 8.9, MS ESI m/z 435 [M+H]+.

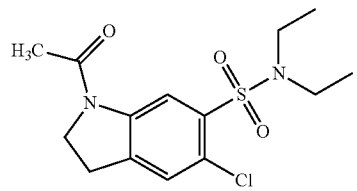 [SMILES: CCN(CC)S(=O)(=O)c1cc2c(cc1Cl)CCN2C(C)=O]

Crude product collected (0.117 g, ≤100%) as an off white solid: mp 178-181° C.; ¹H NMR (500 MHz, CDCl3) δ [sample needs further purification].

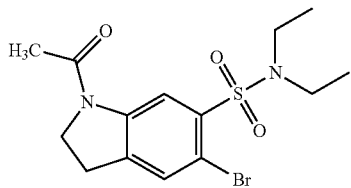

Product collected (0.110 g, 99%) as an off white solid: mp 195-196° C.; ¹H NMR (500 MHz, CDCl3) δ 8.72 (s, 1H), 7.47 (s, 1H), 4.13 (t, J=8.5 Hz, 2H), 3.42 (q, J=7.0 Hz, 4H), 3.23 (t, J=8.0 Hz, 2H), 2.23 (s, 3H), 1.19 (t, J=7.5 Hz, 6H); ¹³C NMR (500 MHz, CDCl3) δ 169.28, 142.7, 139.7, 136.9, 131.6, 118.2, 114.0, 49.2, 42.314, 27.8, 24.3, 14.4, 8.9.

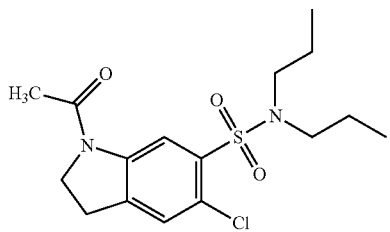 [SMILES: CCCN(CCC)S(=O)(=O)c1cc2c(cc1Cl)CCN2C(C)=O]

Product collected (0.104 g, 85%) as a light brown solid: mp 118-120° C.; ¹H NMR (500 MHz, CDCl3) δ 8.78 (s, 1H), 7.49 (s, 1H), 4.23 (t, J=8.5 Hz, 2H), 3.59 (t, J=6.0 Hz, 4H), 3.53 (t, J=5.5 Hz, 4H), 3.29 (s, 6H), 3.24 (t, J=9.0 Hz, 2H), 2.23 (s, 3H); ¹³C NMR (500 MHz, CDCl3) δ 169.2, 142.1, 137.9, 136.9, 128.0, 126.6, 118.1, 49.9, 49.6, 49.2, 27.9, 24.3, 22.1, 19.6, 11.5, 11.4.

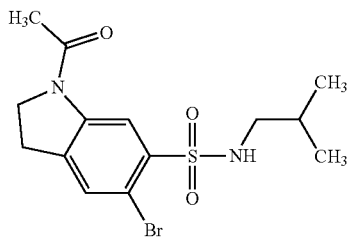 [SMILES: CC(=O)N1CCc2cc(Br)c(S(=O)(=O)NCC(C)C)cc21]

Product collected (0.116 g, ≤100%) as a tan solid: mp 215-220° C.; ¹H NMR (500 MHz, CDCl3) δ 8.87 (s, 1H), 7.47 (s, 1H), 5.13 (t, J=6.5 Hz, 1H), 4.13 (t, J=8.5 Hz, 2H), 3.25 (t, J=9.0 Hz, 2H), 2.70 (t, J=6.5 Hz, 2H), 2.23 (s, 3H), 1.74 (m, 1H), 0.89 (d, J=8.5 Hz, 6H), ¹³C NMR (500 MHz, CDCl3) δ 169.24 143.1 138.2 137.7 130.9 119.2 113.1 50.9 649.2 46.1 28.7 27.8 24.3 8.9

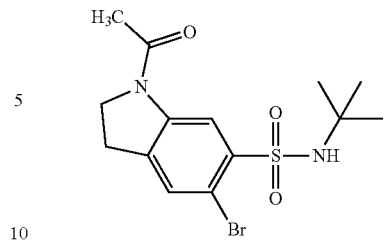

Product collected (0.116 g, ≤100%) as an off white solid: mp 225-230° C.; ¹H NMR (500 MHz, CDCl3) δ 8.82 (s, 1H), 7.45 (s, 1H), 5.07 (s, 1H), 4.23 (t, J=9.0 Hz, 2H), 3.24 (t, J=8.5 Hz, 2H), 2.23 (s, 3H), 1.23 (s, 9H); ¹³C NMR (500 MHz, CDCl3) δ 169.2, 143.1, 141.7, 137.2, 130.8, 118.5, 113.2, 55.2, 49.2, 46.2, 30.3, 27.8, 24.4, 8.9.

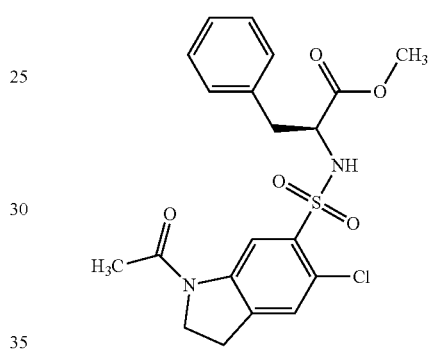

Product collected (0.119 g, 80%) as an orange solid: MS ESI m/z 437 [M+H]+.

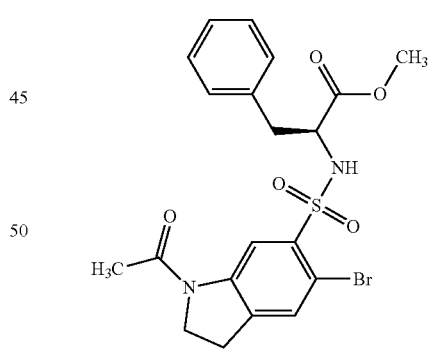

Product collected (0.127 g, 90%) as a tan solid: mp 178-183° C.; ¹H NMR (500 MHz, CDCl3) δ 8.79 (s, 1H), 7.39 (s, 1H), 7.21-7.08 (m, 5H), 5.66 (d, J=8.0 Hz, 1H), 4.26 (dt, J=8.0, 5.8 Hz, 1H), 4.09 (m, 2H), 3.54 (s, 3H), 3.20 (t, J=1.0 Hz, 2H), 3.06 (t, J=4.8 Hz, 2H), 2.21 (m, 3H); ¹³C NMR (500 MHz, CDCl3) δ 171.0, 169.1, 142.9, 138.4, 137.6, 135.2, 131.0, 129.8, 128.8, 127.4, 118.8, 113.7, 57.2, 52.6, 49.2, 39.7, 27.8, 24.3.

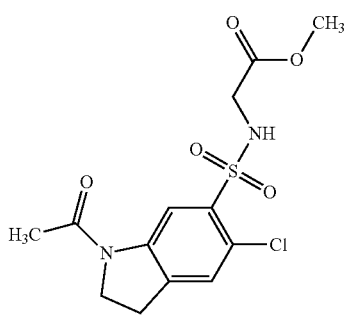 [SMILES: COC(=O)CNS(=O)(=O)c1cc2c(cc1Cl)CCN2C(C)=O]

Crude product collected (0.127 g, ≤100%) as a tan solid. MS ESI m/z 347 [M+H]+.

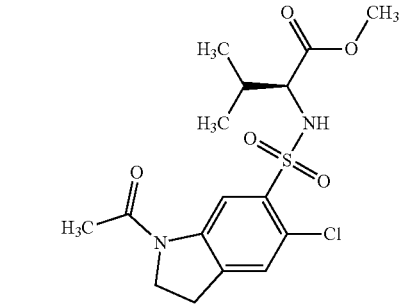

Crude product collected (0.0644 g, 49%) as an orange solid; ¹H NMR (500 MHz, CDCl3) δ [sample needs further purification].

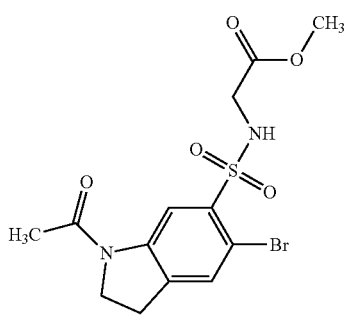 [SMILES: COC(=O)CNS(=O)(=O)c1cc2c(cc1Br)CCN2C(C)=O]

Product collected (0.105 g, 93%) as a tan solid: mp 176-182° C.; ¹H NMR (500 MHz, CDCl3) δ 8.86 (s, 1H), 7.49 (s, 1H), 5.74 (bs, 1H), 4.13 (t, J=8.5 Hz, 2H), 3.82 (d, J=5.5 Hz, 2H), 3.68 (s, 3H), 3.25 (t, J=8.5 Hz, 2H), 2.24 (s, 3H); ¹³C NMR (500 MHz, CDCl3) δ 169.2, 161.8, 143.0, 137.9, 137.7, 131.1, 119.1, 113.7, 49.2, 46.1, 44.6, 24.3, 8.9.

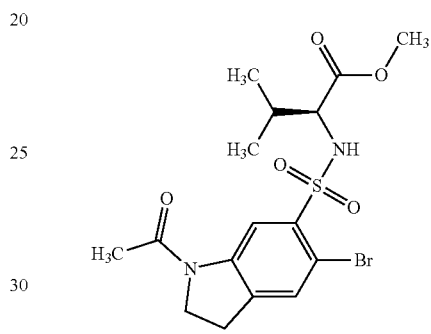

Product collected (0.111 g, 87%) as a tan solid: mp 178-182° C.; ¹H NMR (500 MHz, CDCl3) δ 8.50 (s, 1H), 7.46 (s, 1H), 5.70 (d, J=9.6 Hz, 1H), 4.12 (t, J=7.8 Hz, 2H), 3.83 (dd, J=9.3, 5.1 Hz, 1H), 3.54 (s, 3K), 3.23 (t, J=9.0 Hz, 2H), 2.23 (s, 3H), 2.08 (m, 1H), 0.92 (in, 6H); ¹³C NMR (500 MHz, CDCl3) δ 171.5, 169.2, 142.9, 138.4, 137.7, 130.95, 118.8, 113.8, 61.7, 52.4, 49.2, 32.0, 27.8, 24.3, 19.0, 17.8. MS ESI m/z 389 [M+H]+.

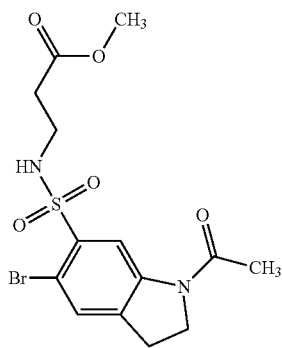 [SMILES: COC(=O)CCNS(=O)(=O)c1cc2c(cc1Br)CCN2C(C)=O]

Product collected (0.117 g, 97%) as an off white solid: mp 190-193° C.; ¹H NMR (500 MHz, CDCl3) δ 8.87 (s, 1H), 7.47 (s, 1H), 5.77 (t, J=6.0 Hz, 1H), 4.11 (t, J=8.5 Hz, 2H), 3.67 (s, 3H), 3.23 (t, J=8.5 Hz, 2H), 3.17 (dd, J=12.0, 6.5 Hz, 2H), 2.50 (t, J=5.5 Hz, 2H), 2.21 (s, 3H); ¹³C NMR (500 MHz, CDCl3) δ 172.5, 169.2, 143.1, 138.3, 137.7, 131.0, 119.1, 113.3, 52.2, 49.2, 39.0, 34.1, 27.8, 24.3.

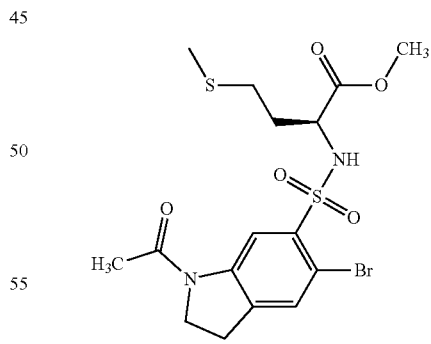

Product collected (0.114 g, 83%) as a light tan solid: mp 117-119° C.; ¹H NMR (500 MHz, CDCl3) δ 8.83 (s, 1H), 7.47 (s, 1H), 5.94 (d, J=8.1 Hz, 1H), 4.13 (t, J=8.5 Hz, 2H), 3.62 (s, 3H), 3.24 (t, J=7.2 Hz, 2H), 2.23 (s, 3H), 2.06 (s, 3H); ¹³C NMR (500 MHz, CDCl3) δ 171.6, 169.2, 1410, 138.1, 131.1, 118.9, 113.7, 55.3, 52.9, 49.2, 32.8, 29.7, 27.8, 24.3, 15.6, 8.9.

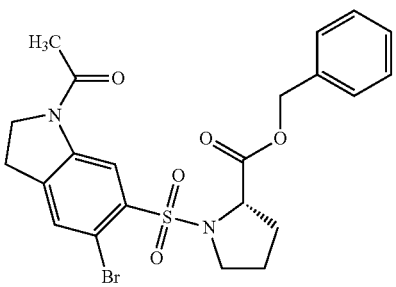 [SMILES: CC(=O)N1CCc2cc(Br)c(S(=O)(=O)N3CCC[C@H]3C(=O)OCc3ccccc3)cc21]

Crude product collected (0.156 g, ≤100%) as a light tan solid: mp 118-120° C.

Example 10. Synthesis of 1-Acetyl-5-bromoindoline-6-Sulfonamide

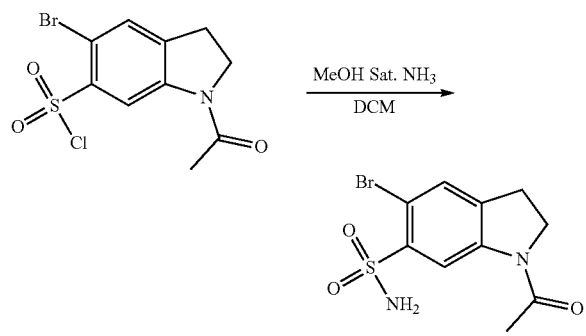

A stirred solution of sulfonyl chloride (500 mg, 1.7 mmol) in DCM (15 mL) and saturated methanolic ammonia (5.0 mL, approx. 35 mmol) was heated until the solids dissolved, and then allowed to return to room temperature. After 30 minutes, the solids were precipitated out by the addition of EtOAc (5 mL) and collected by vacuum filtration, washing with DCM, EtOAc, and petroleum ether, to yield a white solid (313 mg, 66%). 1H NMR (500 MHz, DMSO-$d_6$) δ 8.7 (s, 1H), 7.6 (s, 1H), 7.4 (s, 2H), 4.1 (t, 2H, J=8.5), 3.2 (t, 2H, J=8.75), 2.18 (s, 3H). RF=0.36 (20:80 EtOAc:DCM). MP: 231° C.-decomposed at 254° C.

Example 11. Ninhydrin Assay for DapE

A standard curve was first generated for the Ninhydrin reagent using glutamic acid. Then, the appropriate concentration of glutamic acid in 50 mM, pH 7.5 phosphate buffer were incubated at 37° C. and dispensed into a 1.7 mL Eppendrof tube. Next, 0.33 mL of the reaction was transferred into another 1.7 mL Eppendorf tube. Following, 0.166 mL of 2% Ninhydrin reagent was added to the reaction mixture and then heated in a boiling water bath for 15 min. After cooling in a cold water bath and the addition of 0.83 mL of 50% ethanol aqueous solution, the mixture was vigorously shaken and the absorbance was measured at 570 nm. Results can be found in the table, below.

| Concentration (μM) | Absorbance |
| --- | --- |
| 0 | 0.1 |
| 50 | 0.283 |
| 100 | 0.48 |
| 200 | 0.82 |
| 400 | 1.644 |
| 600 | 2.454 |
| 800 | 3.154 |
| 1000 | 3.977 |
| 1500 | overflow |

The $IC_{50}$ of the inhibitors described herein can be determined using captopril as the standard. To a reaction mixture in 50 mM at pH 7.5 HEPES buffer, containing DapE (0.25 μM), a solution of the inhibitor is added. Next, the reaction mixture is allowed to incubate for 10 minutes. Following, 1 mM of alpha-N-monomethylated SDAP substrate, made by reductive amination of the SDAP substrate with aqueous formaldehyde and sodium cyanoborohydride, was added, and reaction was allowed to incubate for 40 min. Next, 0.33 mL of the reaction solution was transferred into another 1.7 mL Eppendorf tube, 0.166 mL of 2% Ninhydrin reagent was added to the reaction mixture, and the mixture was heated in a boiling water bath for 15 min. The water bath was cooled. The mixture was vigorously shaken and the absorbance was measured at 570 nm. The $IC_{50}$ for captopril (standard) is ca. 0.5 uM.

The compounds disclosed herein can bind to the active site DapE, as evidenced in FIG. 1 by the large negative values of delta G derived using the molecular docking program SwissDock (Grosdidier, A.; Zoete, V.; Michielin, O. *Nucleic Acids Res.* 2011, 39, W270-W277), which indicates that they are capable of inhibiting DapE by blocking the active site. Calculated binding values represent docking modes that were each visually confirmed to represent the inhibitor binding to the active site of the enzyme.

Example 12. Inhibition of NDM-1 Assay

The ability of the compounds described herein to inhibit NDM-1 was determined in the following way.

A Substrate Working Solution was prepared from CRHROMACEF (6 μM) and Tween-20 (0.02% v/v) in water. An Enzyme Working Solution was prepared with NDM-1 (0.5 μg/mL), Hepes (0.1 M), pH 7 and Tween-20 (0.02% v/v). An Inhibitor Working Solution was prepared from 50 mM of the inhibitor in DMSO. The final assay conditions were 1 mL, Hepes (50 mM), pH 7, Tween-20 (0.02% v/v), CHROMACEF (3 uM), Δ35 NDM-1 (0.25 μg/mL). Extra zinc was omitted from these assays because extra ZnSO4 interferes with the metal binding groups in inhibitors.

An aliquot of the Inhibitor Working Solution was added to a polystyrene disposable cuvette to achieve a final concentration of 0-50 μM (in 1 mL final). Supplemental DMSO was added to reach a final volume of 4 μL. NDM-1 Working Solution (0.05 mL) was added to the cuvette and the inhibitor and enzyme were allowed to incubate for about 20 minutes. The reaction was initiated by added 0.5 mL Substrate Working Solution. The solution was mixed quickly, but gently to avoid bubble formation. CHROMACEF 6 M was recorded to start the reaction. The reaction was mixed fast, but gently. The change in absorbance $\Delta Abs_{442nm/min}$ was measured for each inhibitor from the linear slope from each inhibitor concentration.

The percent inhibition of inhibitors described herein are shown in the table, below.

| Structure | % NMD-1 Inhibition (5 μM) |
|---|---|
| 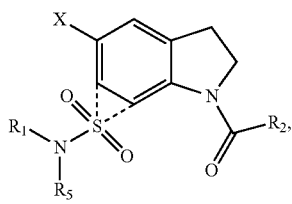 | 16.8 |
| 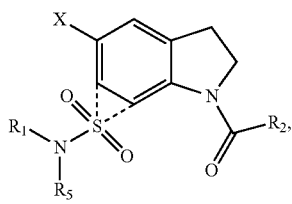 | 62.7 |
| 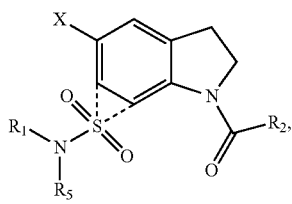 | 27.3 |

What is claimed:

1. A method of inhibiting bacterial metallo-β-lactamase in a cell comprising contacting the cell with a compound of Formula (III):

(III)

wherein
the dashed lines indicate that the sulfonamide moiety can be attached to either the 6-position or the 7-position of the indoline sulfonamide compound;
$R_1$ is H, $C_{1-6}$alkyl, $OC_{1-6}$alkyl, $C_{3-8}$cycloalkyl, $C_{3-8}$heterocycloalkyl, $C_{1-6}$alkylene$R_6$, (C=O)$C_{1-6}$alkyl, aryl, or heteroaryl;
$R_2$ is $C_{1-6}$ alkyl or O—$C_{1-4}$alkylene$R_6$;
$R_5$ is H, $C_{1-8}$alkyl, $C_{1-6}$alkylene$R_6$, or $C_{3-8}$cycloalkyl, or $R_1$ and $R_5$ are taken together with the nitrogen to which they are attached to form a 5- to 7-membered ring;
$R_6$ is H aryl, (C=O)OH, (C=P)O$C_{1-3}$alkyl, O$C_{1-3}$alkyl, S$C_{1-3}$alkyl, O(C=O)$C_{1-3}$alkyl; and
X is I, Br, Cl, F, or H.

2. The method of claim 1, wherein the compound of Formula (III) comprises a compound of Formula (IIIA):

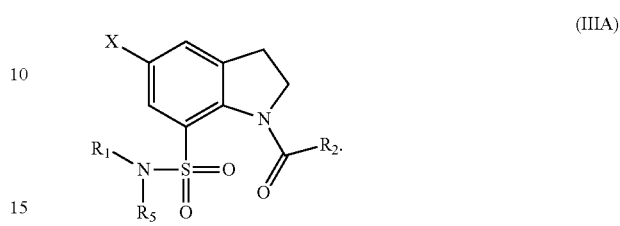

(IIIA)

3. The method of claim 1, wherein the compound of Formula (III) comprises a compound of Formula (IIIB):

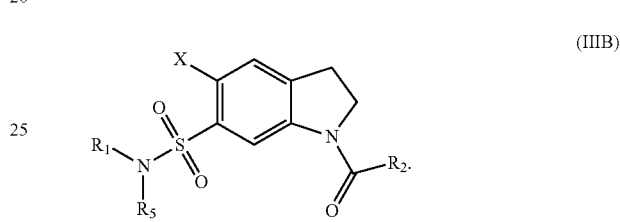

(IIIB)

4. The method of claim 1, wherein X is H, Cl, or Br.

5. The method of claim 1, wherein $R_2$ is methyl, ethyl, or $OCH_2$-phenyl.

6. The method of claim 1, wherein $R_5$ is selected from the group consisting of:
   (i) H;
   (ii) methyl, ethyl, or n-propyl;
   (iii) $CH_2$-phenyl;
   (iv) $OCH_2CH_2OCH_3$;
   (v) $CH_2COOCH_3$; and
   (vi) cyclopentyl or cyclohexyl;
   or $R_1$ and $R_5$ are taken together with the nitrogen to which they are attached to form a 5- to 7-membered ring selected from pyrrolidine, piperidine, azepane, and indoline.

7. The method of claim 1, wherein $R_1$ is selected from the group consisting of H, methyl, ethyl, n-propyl, n-butyl, tert-butyl, n-hexyl, isopentyl, cyclopentyl, cyclohexyl, piperidinyl, $OCH_3$, $CH_2$-phenyl, (C=O)OH, $(CH_2)_5COOH$, $CH_2$(C=O)$OCH_3$, $CH_2CH_2$(C=O)$OCH_3$, CH(iPr)(C=O)$OCH_3$, CH($CH_2$-phenyl)(C=O)$OCH_3$, CH($CH_2CH_2SCH_3$)(C=O)$OCH_3$, $CH_2CH_2OCH_3$, $CH_2CH_2SCH_3$, (C=O)$CH_3$, phenyl, methylpyridine, pyrazine, pyrimidine, isothiazole, and benzothiazole.

8. The method of claim 2, wherein the compound of Formula (IIIA) is selected from the group consisting of

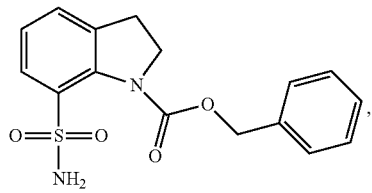

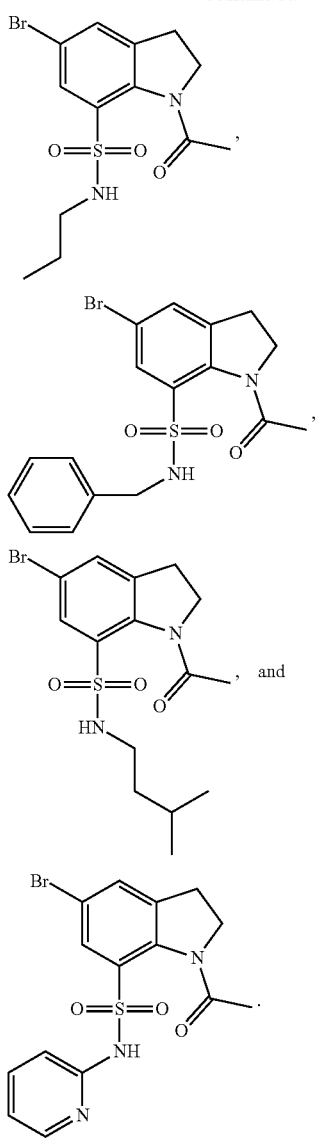
9. The method of claim 3, wherein the compound of Formula (IIIB) is selected from the group consisting of:
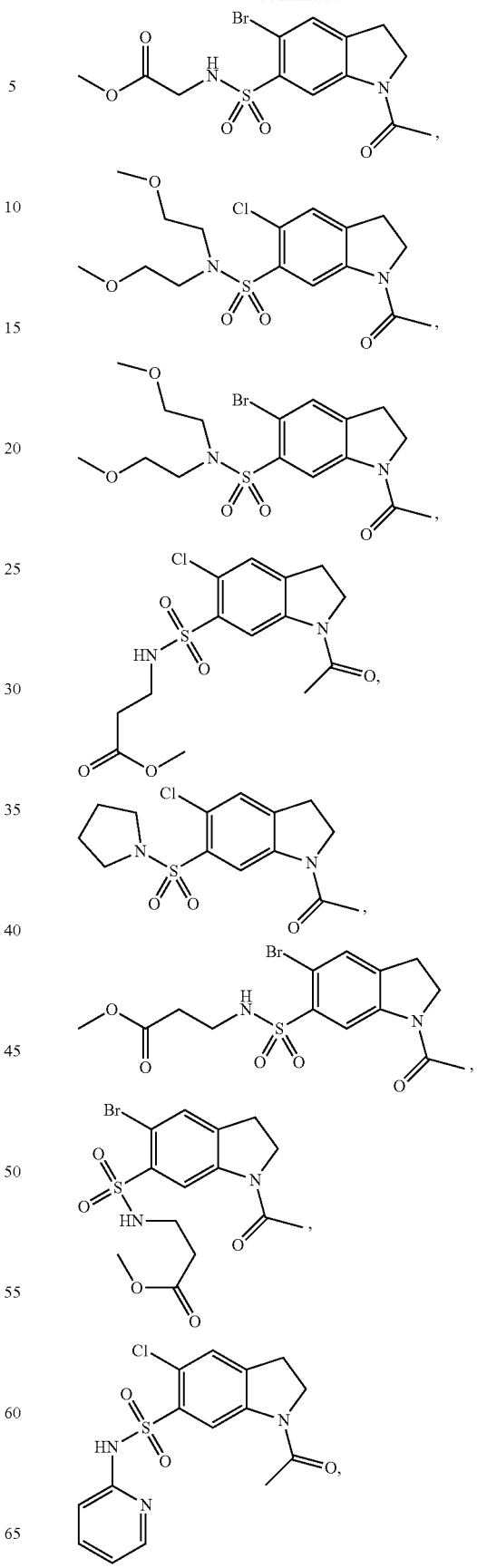

67
-continued
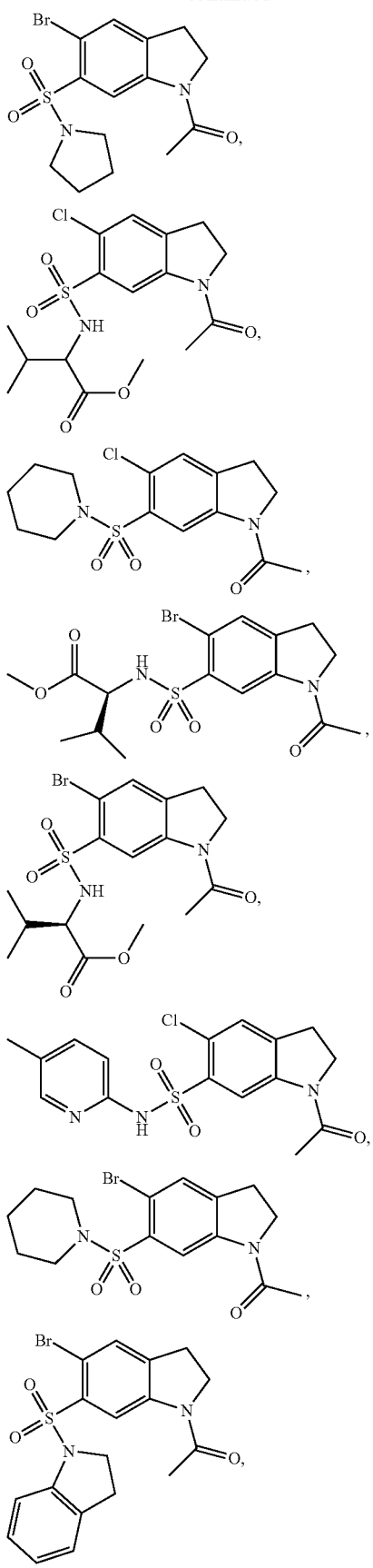
68
-continued
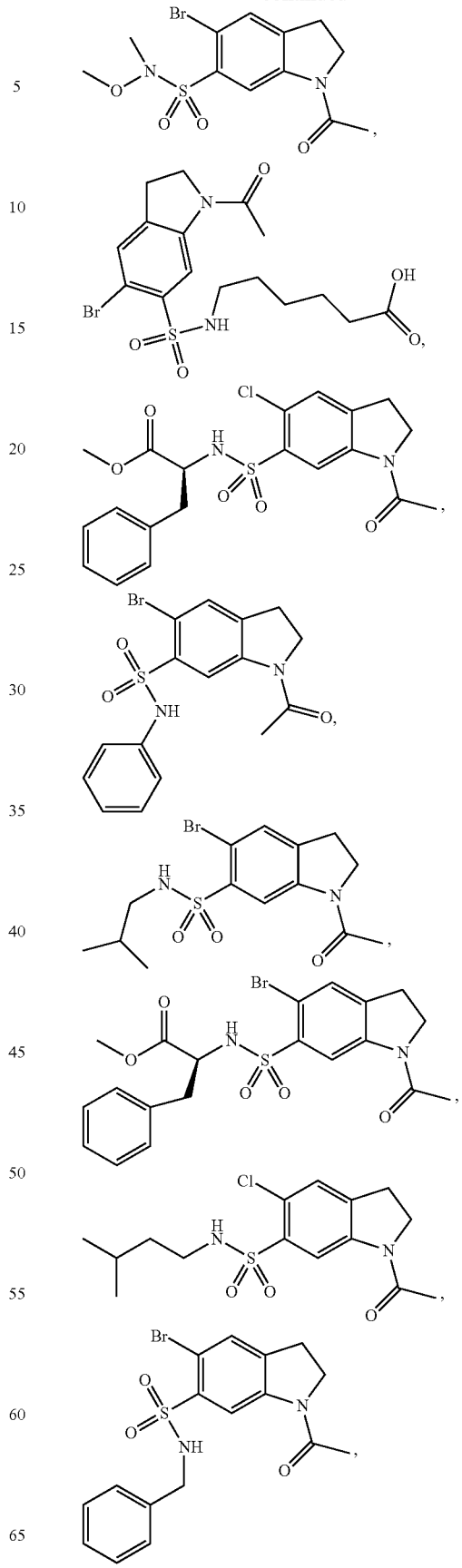

-continued
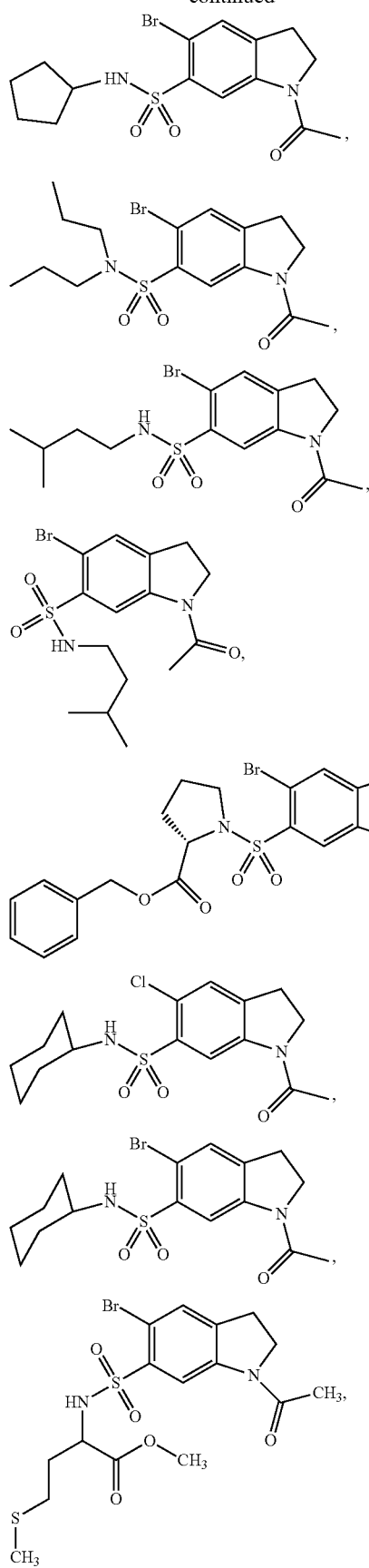
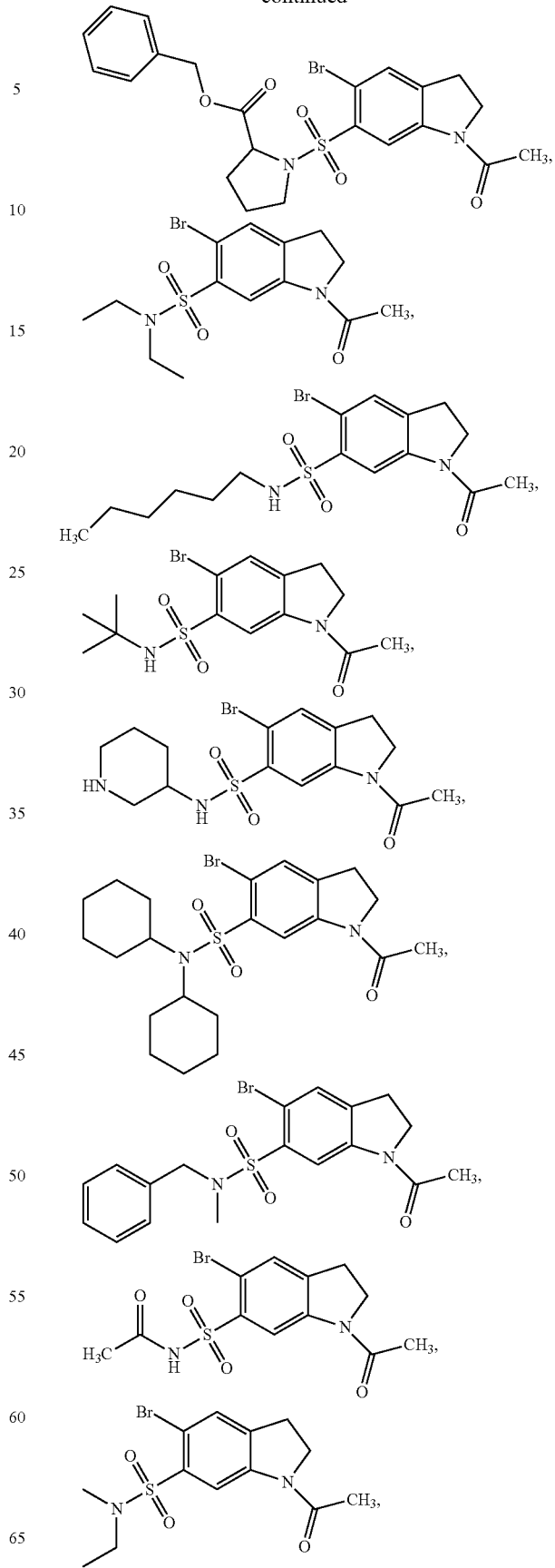

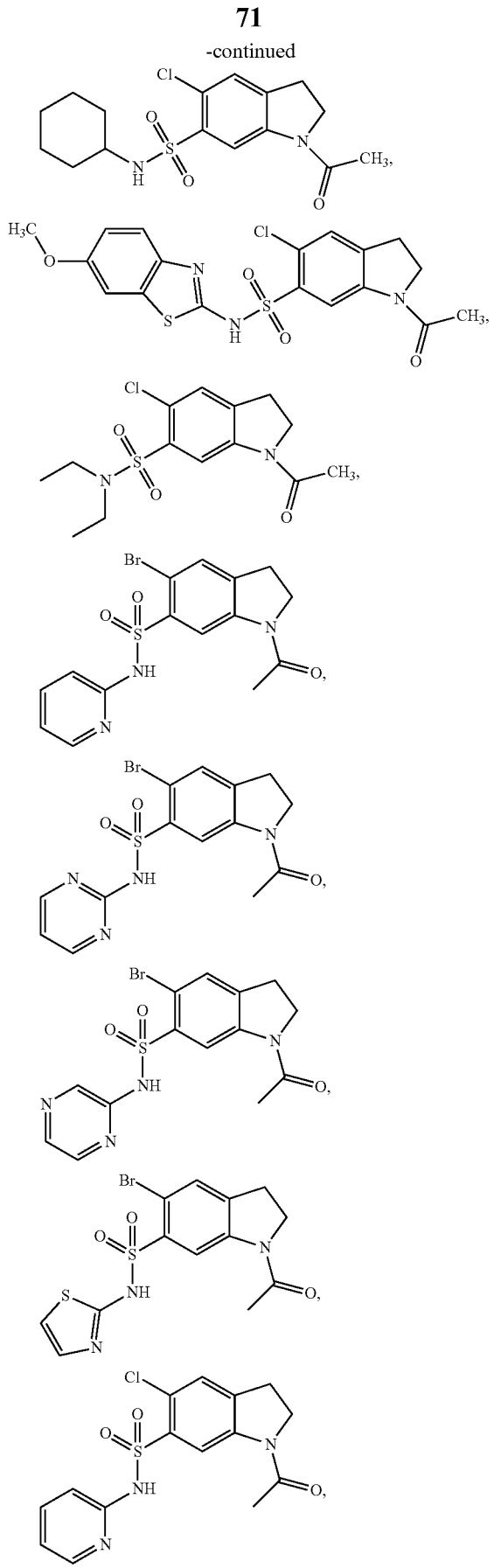

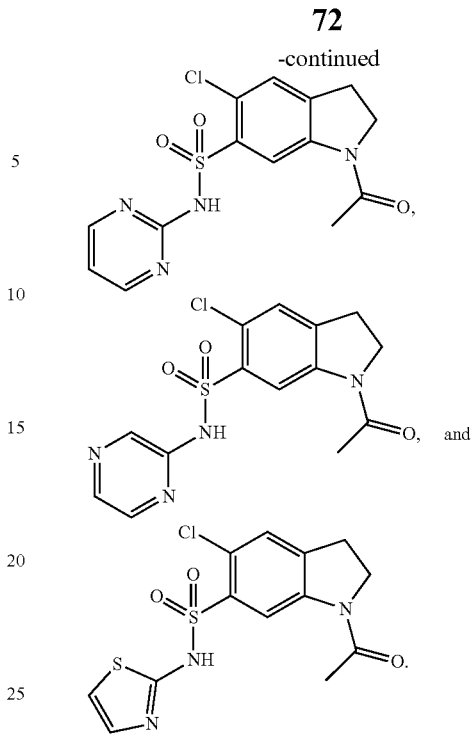

10. The method of claim 1, wherein the metallo-β-lactamase is selected from the group consisting of NDM-1, IMP-1, and VIM-2.

11. The method of claim 10, wherein the metallo-β-lactamase is NDM-1.

12. The method of claim 1, wherein the contacting occurs in vivo.

13. The method of claim 1, wherein the contacting comprises administering to a subject in need thereof.

14. The method of claim 13, wherein the subject suffers from bacterial infection.

15. A method of treating a disease or condition wherein inhibition of metallo-β-lactamase provides a benefit, comprising administering a therapeutically effective amount of a compound of Formula (III), or a pharmaceutically acceptable salt thereof:

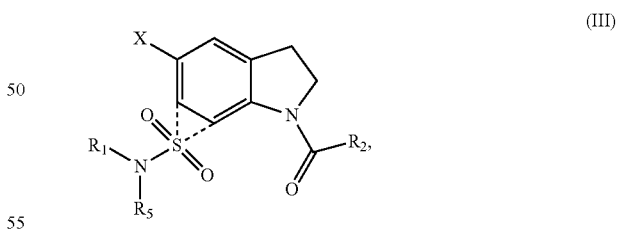

(III)

wherein
the dashed lines indicate that the sulfonamide moiety can be attached to either the 6-position or the 7-position of the indoline sulfonamide compound;
$R_1$ is H, $C_{1-8}$alkyl, $OC_{1-8}$alkyl, $C_{3-8}$cycloalkyl, $C_{3-8}$heterocycloalkyl, $C_{1-8}$alkylene$R_6$, $(C=O)C_{1-8}$alkyl, aryl, or heteroaryl;
$R_2$ is $C_{1-6}$ alkyl or O—$C_{1-4}$alkylene$R_6$;
$R_5$ is H, $C_{1-8}$alkyl, $C_{1-8}$alkylene$R_8$, or $C_{3-8}$cycloalkyl, or $R_1$ and $R_5$ are taken together with the nitrogen to which they are attached to form a 5- to 7-membered ring;

$R_6$ is H aryl, (C=O)OH, (C=O)OC$_{1-3}$alkyl, SC$_{1-3}$alkyl, O(C=O)C$_{1-3}$alkyl; and X is I, Br, Cl, F, or H.

16. The method of claim 15, wherein the metallo-β-lactamase is selected from the group consisting of NDM-1, IMP-1, and VIM-2.

17. The method of claim 16, wherein the metallo-β-lactamase is NDM-1.

18. The method of claim 15 further comprising administering a therapeutically effective amount of a second therapeutic agent useful in the treatment of the disease or condition.

19. The method of claim 15, wherein the second therapeutic agent is a β-lactam antibiotic.

20. The method of claim 15, wherein the disease or condition is a bacterial infection.

* * * * *

UNITED STATES PATENT AND TRADEMARK OFFICE
CERTIFICATE OF CORRECTION

PATENT NO. : 11,021,469 B2
APPLICATION NO. : 16/514921
DATED : June 1, 2021
INVENTOR(S) : Daniel Paul Becker et al.

Page 1 of 1

It is certified that error appears in the above-identified patent and that said Letters Patent is hereby corrected as shown below:

In the Claims

At Column 63, Line 61, in Claim 1, "$C_{1-6}$alkyl," should be -- $C_{1-8}$alkyl, --.

At Column 64, Line 1, in Claim 1, "(C=P)$OC_{1-3}$alkyl," should be -- (C=O)$OC_{1-3}$alkyl, --.

At Column 66, Lines 47-55, in Claim 9, " 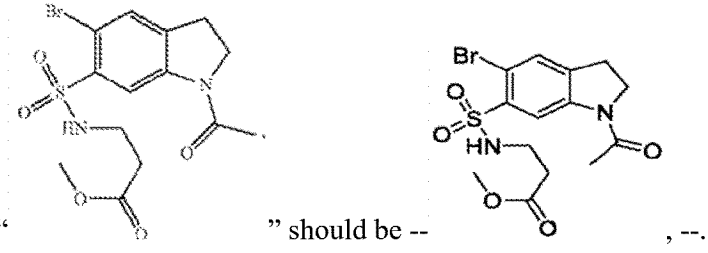 " should be --  , --.

At Column 72, Line 61, in Claim 15, "$OC_{1-8}$alkyl," should be -- $OC_{1-6}$alkyl, --.

At Column 72, Line 62, in Claim 15, "$C_{1-8}$alkylene$R_6$, (C=O)$C_{1-8}$alkyl," should be -- $C_{1-6}$alkylene$R_6$, (C=O)$C_{1-6}$alkyl, --.

At Column 72, Line 65, in Claim 15, "$C_{1-8}$alkylene$R_8$," should be -- $C_{1-6}$alkylene$R_6$, --.

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*